(12) United States Patent
Foote

(10) Patent No.: US 10,307,561 B2
(45) Date of Patent: Jun. 4, 2019

(54) VENT ARRANGEMENT FOR RESPIRATORY DEVICE

(71) Applicant: ResMed Limited, Bella Vista (AU)

(72) Inventor: Roger Mervyn Lloyd Foote, Sydney (AU)

(73) Assignee: ResMed Limited (AU)

( * ) Notice: Subject to any disclaimer, the term of this patent is extended or adjusted under 35 U.S.C. 154(b) by 659 days.

(21) Appl. No.: 14/776,352

(22) PCT Filed: Mar. 14, 2014

(86) PCT No.: PCT/AU2014/000263
§ 371 (c)(1),
(2) Date: Sep. 14, 2015

(87) PCT Pub. No.: WO2014/138803
PCT Pub. Date: Sep. 18, 2014

(65) Prior Publication Data
US 2016/0074618 A1     Mar. 17, 2016

(30) Foreign Application Priority Data

Mar. 14, 2013 (AU) .................................. 2013900885
Aug. 16, 2013 (AU) .................................. 2013903088

(51) Int. Cl.
*A61M 16/00* (2006.01)
*A61M 16/20* (2006.01)
(Continued)

(52) U.S. Cl.
CPC ........ *A61M 16/20* (2013.01); *A61M 16/0003* (2014.02); *A61M 16/0066* (2013.01);
(Continued)

(58) Field of Classification Search
CPC .... A61M 16/20; A61M 16/003; A61M 16/00; A61M 16/0066; A61M 16/06;
(Continued)

(56) References Cited

U.S. PATENT DOCUMENTS 1,407,216 A  2/1922 Potter
3,101,736 A  8/1963 Egger
(Continued)

FOREIGN PATENT DOCUMENTS

EP  1327458 A1  7/2003
EP  2705869 A2  3/2014
(Continued)

OTHER PUBLICATIONS

International Search Report and Written Opinion for Application No. PCT/US2012/055148 dated Feb. 15, 2013.
(Continued)

*Primary Examiner* — Steven O Douglas
(74) *Attorney, Agent, or Firm* — Botos Churchill IP Law LLP

(57) ABSTRACT

A vent arrangement for a respiratory pressure therapy device may include one or a plurality of vents configured with a variable aperture for communicating a flow of breathable gas. The vent arrangement may be configured with a cross section profile exposed to the flow of breathable gas communicating through the vent that does not change as the aperture size changes. A vent arrangement may include a plurality of the vents and the aperture size of each vent may be controlled independently or together, and may be controlled according to one or more input signals from one or more sensors. Examples of suitable input signals include flow, pressure, noise, accelerometer outputs, orientation of a patient or presence of any obstructions. A patient interface or an air circuit may include the vent arrangement, or the vent
(Continued)

arrangement may be configured to connect with a patient interface or an air circuit.

25 Claims, 32 Drawing Sheets

(51) Int. Cl.
| | |
|---|---|
| *A61M 16/06* | (2006.01) |
| *F16K 3/03* | (2006.01) |
| *A61M 16/16* | (2006.01) |
| *A61M 16/10* | (2006.01) |

(52) U.S. Cl.
CPC .......... *A61M 16/024* (2017.08); *A61M 16/06* (2013.01); *F16K 3/03* (2013.01); *A61M 16/107* (2014.02); *A61M 16/16* (2013.01); *A61M 2016/0027* (2013.01); *A61M 2016/0033* (2013.01); *A61M 2205/332* (2013.01); *A61M 2205/3334* (2013.01); *A61M 2205/3365* (2013.01); *A61M 2205/3375* (2013.01); *A61M 2205/42* (2013.01); *A61M 2205/505* (2013.01)

(58) Field of Classification Search
CPC .. A61M 2205/3334; A61M 2205/3365; A61M 2205/3375; A61M 2016/0033; A61M 2016/0027; A61M 16/16; A61M 2205/42; A61M 2205/505; A61M 16/107; A61M 2205/332; F16K 3/03
See application file for complete search history.

(56) References Cited

U.S. PATENT DOCUMENTS

| | | | |
|---|---|---|---|
| 4,094,492 A | 6/1978 | Beeman et al. | |
| 4,306,567 A | 12/1981 | Krasner | |
| 4,782,832 A | 11/1988 | Trimble et al. | |
| 4,796,619 A | 1/1989 | Walther | |
| 4,842,245 A | 6/1989 | Kelsey | |
| 5,370,154 A | 12/1994 | Greer | |
| 5,568,910 A | 10/1996 | Koehler et al. | |
| 6,426,716 B1 | 7/2002 | McEwan | |
| 6,446,629 B1 | 9/2002 | Takaki et al. | |
| 6,581,594 B1 | 6/2003 | Drew et al. | |
| 6,581,596 B1 | 6/2003 | Truitt et al. | |
| 6,659,101 B2 | 12/2003 | Berthon-Jones | |
| 6,722,359 B2 | 4/2004 | Chalvignac | |
| 6,745,770 B2 | 6/2004 | McAuliffe et al. | |
| 7,059,325 B2 | 6/2006 | Hollis | |
| 8,528,562 B2 * | 9/2013 | Smith .................. | A61M 16/06 128/204.26 |
| 2001/0009153 A1 * | 7/2001 | Pessala ............. | A61M 16/0051 128/204.23 |
| 2003/0075176 A1 | 4/2003 | Fukunaga et al. | |
| 2004/0007232 A1 | 1/2004 | Rochat | |
| 2004/0144383 A1 | 7/2004 | Thomas et al. | |
| 2005/0126648 A1 | 6/2005 | Vu et al. | |
| 2006/0060200 A1 | 3/2006 | Ho et al. | |
| 2006/0090762 A1 | 5/2006 | Hegde et al. | |
| 2007/0033793 A1 | 2/2007 | Schlosser et al. | |
| 2008/0047560 A1 | 2/2008 | Veliss et al. | |
| 2008/0283060 A1 | 11/2008 | Bassin | |
| 2008/0302364 A1 | 12/2008 | Garde et al. | |
| 2009/0044808 A1 | 2/2009 | Guney et al. | |
| 2009/0050156 A1 | 2/2009 | Ng et al. | |
| 2009/0203972 A1 | 8/2009 | Heneghan et al. | |
| 2009/0260631 A1 | 10/2009 | Aubonnet et al. | |
| 2010/0000534 A1 | 1/2010 | Kooij et al. | |
| 2010/0043796 A1 | 2/2010 | Meynink et al. | |
| 2010/0051034 A1 | 3/2010 | Howard et al. | |
| 2010/0258123 A1 | 10/2010 | Somaiya et al. | |
| 2010/0307500 A1 | 12/2010 | Armitstead | |
| 2010/0326447 A1 | 12/2010 | Loomas et al. | |
| 2011/0126832 A1 | 6/2011 | Winter et al. | |
| 2012/0065533 A1 | 3/2012 | Carrillo, Jr. et al. | |
| 2013/0213401 A1 * | 8/2013 | Haibach ................ | A61M 16/06 128/205.25 |
| 2014/0283831 A1 * | 9/2014 | Foote .................. | A61M 16/026 128/204.19 |

FOREIGN PATENT DOCUMENTS

| | | |
|---|---|---|
| WO | 1998004310 A1 | 2/1998 |
| WO | 1998034665 A1 | 8/1998 |
| WO | 2000/078381 A1 | 12/2000 |
| WO | 0126722 A1 | 4/2001 |
| WO | 2002/053217 | 7/2002 |
| WO | 2004/073778 A1 | 9/2004 |
| WO | 2005051468 A1 | 6/2005 |
| WO | 2005/063328 A1 | 7/2005 |
| WO | 2006/074513 A1 | 7/2006 |
| WO | 2006/102708 A1 | 10/2006 |
| WO | 2006130903 A1 | 12/2006 |
| WO | 2008/055308 | 5/2008 |
| WO | 2009/052560 A1 | 4/2009 |
| WO | 2010/135785 A1 | 12/2010 |
| WO | 2011006199 A1 | 1/2011 |
| WO | 2012012835 A2 | 2/2012 |
| WO | 2013040198 A2 | 3/2013 |

OTHER PUBLICATIONS

International Search Report for Application No. PCT/AU2014/000263 dated Jun. 11, 2014.
International Written Opinion for Application PCT/AU2014/000263 dated Jun. 11, 2014.
Partial European Search Report for Application No. 13183779.1 dated Dec. 11, 2013.
U.S. Appl. No. 61/226,069, filed Jul. 16, 2009.
U.S. Appl. No. 61/369,247, filed Jul. 30, 2010.

* cited by examiner

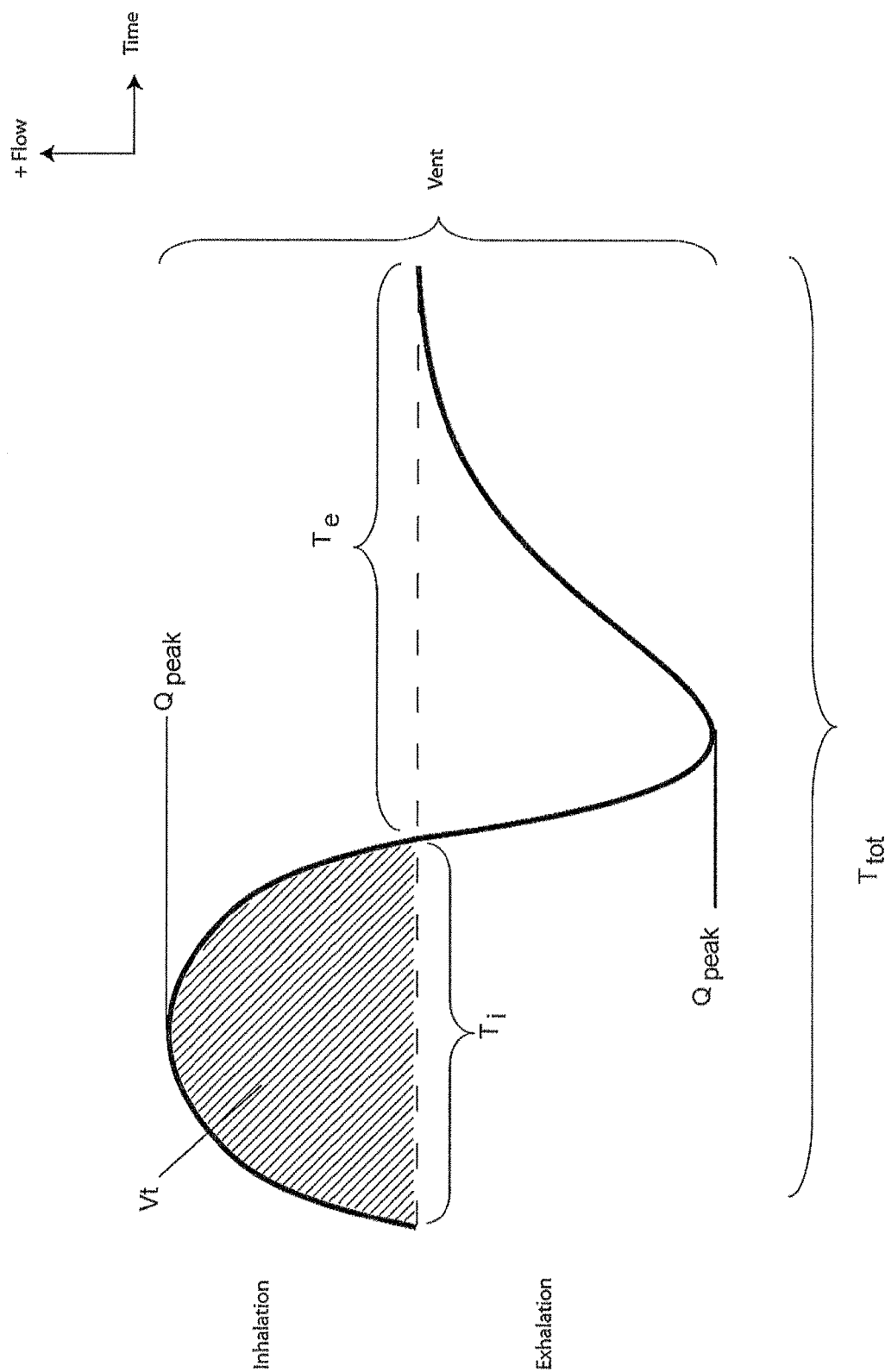

VENT ARRANGEMENT FOR RESPIRATORY DEVICE

CROSS-REFERENCE TO RELATED APPLICATIONS

The present application is a national phase entry under 35 U.S.C. § 371 of International Application No. PCT/AU2014/000263 filed Mar. 14, 2014, published in English, which claims priority from Australian Provisional Patent Application No. 2013900885, filed Mar. 14, 2013 and Australian Provisional Patent Application No. 2013903088, filed Aug. 16, 2013, all of which are hereby incorporated herein by reference.

BACKGROUND OF THE INVENTION (1) Field of the Invention

The present technology relates to one or more of the detection, diagnosis, treatment, prevention and amelioration of respiratory-related disorders. In particular, the present technology relates to medical devices or apparatus, and their use.

(2) Description of the Related Art 3.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Some examples of respiratory disorders include: Obstructive Sleep Apnea (OSA), Cheyne Stokes Respiration (CSR), Obesity Hyperventilation Syndrome (OHS), Chronic Obstructive Pulmonary Disease (COPD), Neuromuscular Disease (NMD) or chest wall disorders.

Otherwise healthy individuals may take advantage of systems and devices to prevent respiratory disorders from arising.

3.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

3.2.3 Systems

A treatment system may comprise a Respiratory Pressure Therapy Device (RPT device), an air circuit, a humidifier, a patient interface, and data management.

3.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cm H2O. For other forms of therapy, such as the delivery of oxygen, the patient interface may not include a seal sufficient to facilitate delivery to the airways of a supply of gas at a positive pressure of about 10 cm H2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from beimg one or more of obtrusive, aesthetically undesirable, costly, poorly fitting, difficult to use and uncomfortable especially when worn for long periods of time or when a patient is unfamiliar with a system. For example, masks designed solely for aviators, mask designed as part of personal protection equipment (e.g. filter masks), SCUBA masks or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

3.2.4.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both flares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam. Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

3.2.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

3.2.4.3 Vent Technologies

Some forms of patient interface systems may include a vent to allow the washout of exhaled carbon dioxide. Many such vents are noisy. Others may block in use and provide insufficient washout. Some vents may be disruptive of the sleep of a bed-partner 1100 of the patient 1000, e.g. through noise or focussed airflow.

ResMed Limited has developed a number of improved mask vent technologies. See WO 1998/034,665; WO 2000/078,381; U.S. Pat. No. 6,581,594; US Patent Application; US 2009/0050156; US Patent Application 2009/0044808.

Table of noise of prior masks (ISO 17510-2: 2007, 10 cmH$_2$O pressure at 1 m)

| Mask name | Mask type | A-weighted sound power level dbA (uncertainty) | A-weighted sound pressure dbA (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |

-continued

Table of noise of prior masks (ISO 17510-2: 2007, 10 cmH₂O pressure at 1 m)

| Mask name | Mask type | A-weighted sound power level dbA (uncertainty) | A-weighted sound pressure dbA (uncertainty) | Year (approx.) |
|---|---|---|---|---|
| ResMed Mirage FX | nasal | 26 (3) | 18 (3) | 2010 |
| ResMed Mirage Swift (*) | nasal pillows | 37 | 29 | 2004 |
| ResMed Mirage Swift II | nasal pillows | 28 (3) | 20 (3) | 2005 |
| ResMed Mirage Swift LT | nasal pillows | 25 (3) | 17 (3) | 2008 |

((*) one specimen only, measured using test method specified in ISO3744 in CPAP mode at 10 cmH₂O)

Sound pressure values of a variety of objects are listed below

| Object | A-weighted sound pressure dBA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3.2.5 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD. RPT devices have also been known as flow generators.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors and a microprocessor-based controller. A blower may include a servo-controlled motor, a volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

Table of noise output levels of prior devices (one specimen only, measured using test method specified in ISO3744 in CPAP mode at 10 cmH₂O).

| Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

3.2.6 Humidifier

Delivery of a flow of breathable gas without humidification may cause drying of airways. Medical humidifiers are used to increase humidity and/or temperature of the flow of breathable gas in relation to ambient air when required, typically where the patient may be asleep or resting (e.g. at a hospital). As a result, a medical humidifier is preferably small for bedside placement, and it is preferably configured to only humidify and/or heat the flow of breathable gas delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a flow generator or RPT device and the patient interface produces humidified gas that minimizes drying of the nasal mucosa and increases patient airway comfort. In addition, in cooler climates warm air applied generally to the face area in and about the patient interface is more comfortable than cold air.

Respiratory humidifiers are available in many forms and may be a standalone device that is coupled to a respiratory apparatus via an air circuit, is integrated with or configured to be coupled to the relevant respiratory apparatus. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a CounterStream™ technology that directs the air flow over a large surface area in a first direction whilst supplying heated water to the large surface area in a second opposite direction. The ResMed HumiCare™ D900 humidifier may be used with a range of invasive and non-invasive ventilators.

BRIEF SUMMARY OF THE TECHNOLOGY

The present technology relates to devices that may be used medically such as for the diagnosis, amelioration, treatment, and/or prevention of respiratory disorders, and may have one or more features for improved comfort, cost, efficacy, ease of use and/or manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology includes a vent, the vent may be configurable with a variable aperture size for communicating a flow of breathable gas. Another aspect of the present technology involves the features of a vent such that the cross section profile exposed to the flow of breathable gas traversing through the vent remains constant even as the vent aperture size changes.

Another form of the present technology comprises a vent arrangement comprising a plurality of vents. Another key aspect of this form of the present technology is that the aperture size of each vent may be controlled independently or together. Furthermore, the aperture size of each vent may be controlled according to one or more input signals from one or more sensors, suitable examples of the one or more sensors may include flow, pressure, noise, accelerometer outputs, orientation of a patient or presence of any obstructions.

Another aspect of one form of the present technology is the control of size of cross-section areas of a plurality of vents according to one or more input signals from one or more sensors. Examples of suitable input signals include flow, pressure, noise, accelerometer outputs, orientation of a patient or presence of any obstructions.

Another aspect of one form of the present technology is a vent arrangement comprising a plurality of vents, and a plurality of microphones, each vent comprising a variable cross-section area for communication of a flow of breathable to gas and the microphones configured to produce signals indicating the noise level generated by a flow of breathable gas communicating through each vent, wherein the cross-section area of each vent is controlled according to the signals produced by the microphones.

Another aspect of one form of the present technology is a vent arrangement comprising a plurality of vents and an accelerometer, each vent comprising a variable cross-section area for communication of a flow of breathable gas and the accelerometer configured to produce a signal indicating orientation of the patient or the orientation of the vent arrangement, wherein the cross-section area of each vent is controlled according to the signal produced by the accelerometer.

Another aspect of one form of the present technology is a vent arrangement comprising a plurality of vents, each vent comprising a variable cross-section area for communication of a flow of breathable gas, wherein the cross-section area of each vent is controlled according to an output from a pressure sensor, wherein the pressure sensor is measuring a pressure of the flow of breathable gas delivered to the patient.

Another aspect of one form of the present technology is a vent arrangement comprising a plurality of vents, each vent comprising a variable cross-section area for communication of a flow of breathable gas, wherein the cross-section area of each vent is controlled according to an output from a flow sensor, wherein the flow sensor is measuring a flow rate of the flow of breathable gas delivered to the patient.

Another aspect of one form of the present technology is a vent arrangement comprising a plurality of vents, each vent comprising a variable cross-section area for communication of a flow of breathable gas, wherein the cross-section area of each vent is controlled according to an aspect of the patient's breath waveform.

A yet another aspect of the current technology is a patient interface comprising a vent arrangement.

A yet another aspect of the current technology is an air circuit comprising a vent arrangement.

A yet another aspect of the current technology is a vent arrangement configured to couple with an air circuit or a patient interface.

Some versions of the present technology include a gas washout vent arrangement for exhausting a flow of exhaust gas received within a patient interface. The gas washout vent arrangement may include one or more vents to exhaust a flow of exhaust gas received within a patient interface, the one or more vents adapted to provide a plurality of different venting configurations. It may further include a sensor adapted to generate a signal indicative of disruption attributable to the exhaust gas. The one or more vents are adjustable to one of the plurality of different venting configurations based on the signal.

In some cases, the one or more vents may be configured for continuous adjustment while the patient interface is in use. The one or more vents may adjust to vary direction of the flow of exhausted gas. The one or more vents may adjust to vary velocity of the flow of exhausted gas. In some cases, the signal may be based on a measured noise level. The signal may be based on detected orientation of the patient interface.

In some examples, the one or more vents may adjust to vary one or more flow impedances of the one or more vents. The one or more vents may adjust by actuating movement of a movable portion of the one or more vents. In some examples, at least a portion of the gas washout vent arrangement may be located in a patient interface. At least a portion of the gas washout vent arrangement may be located in an air circuit. At least a portion of the gas washout vent arrangement may be located in a shell of the patient interface. At least a portion of the gas washout vent arrangement may be located in a decoupling structure of the patient interface. At least a portion of the gas washout vent arrangement may be structured to be coupled with the patient interface.

In some examples, the gas washout vent arrangement may include a controller, such as a processor. The controller may be configured to selectively adjust the vent arrangement based on a detected vent noise to increase an exhaust area of a first vent and decrease an exhaust area of a second vent. The controller may be configured to selectively adjust the vent arrangement based on a detected orientation of the patient interface to increase an exhaust area of a first vent and decrease an exhaust area of a second vent.

The present technology may include apparatus for treating a respiratory disorder. The apparatus may include a patient interface for delivering a supply of air or breathable gas to the entrance of a patient's airways. The apparatus may also include a flow generator for supplying the supply of air or breathable gas to the patient interface. The apparatus may also include a gas washout vent arrangement such as any of the arrangements previously described or described in more detail hereafter. The apparatus may include a controller configured to receive the signal from the sensor and generate one or more signals to adjust the one or more vents in response to the signal indicative of disruption.

Some versions of the present technology may include a control method, such as a control method of an apparatus for adjusting a flow of exhaust gas from a patient interface. The control method may include generating with a sensor a signal indicative of disruption attributable to a flow of exhaust gas through one or more vents from a patient interface. The one or more vents may be adapted for a plurality of different venting configurations. The control method may further include adjusting with a controller the one or more vents to one of the plurality of different venting configurations based on the signal, whereby disruption to a user and/or bed-partner of the user may be reduced.

In some cases of the method, the one or more vents may be adapted for continuous adjustment while the patient interface is in use. The adjusting of the one or more vents to one of the plurality of different venting configurations may change a characteristic of the flow of exhaust gas. The characteristic may be direction of the flow of exhausted gas. The characteristic may be velocity of the flow of exhausted gas. In some cases, the signal may be generated based on a measured noise level. In some cases, the signal maybe generated based on detected orientation of the patient interface. The adjusting the one or more vents to one of the plurality of different venting configurations may include actuating movement of a movable portion of the one or more vents. In some cases, the controller may selectively adjust the one or more vents based on detected vent noise to increase an exhaust area of a first vent and decrease an exhaust area of a second vent. The controller may selectively adjust the one or more vents based on detected orientation of the patient interface to increase an exhaust area of a first vent and decrease an exhaust area of a second vent.

Some embodiments of the present technology may include an apparatus, such as a patient interface, for applying or delivering a flow of breathable gas to an airway of user. The apparatus may include a plenum chamber adapted for coupling with a flow generator or respiratory pressure therapy device to a supply breathable gas to the plenum chamber. The plenum chamber may be further adapted to couple with an airway of a user. The apparatus may also include one or more exhaust vents. The exhaust vents may be coupled with the plenum chamber to permit a flow of exhaust gas from a cavity of the plenum chamber. The one or more exhaust vents may be configured to change a direction of exhaust flow relative to the plenum chamber in accordance with orientation of the plenum chamber such as a change in orientation of the plenum chamber.

The one or more exhaust vents may be configured to enforce an upward flow of exhaust from the plenum chamber upon a changing orientation of the plenum chamber. The one or more exhaust vents may be configured to reduce an exhaust flow in a direction of a bed partner upon a changing orientation of the plenum chamber. The one or more exhaust vents may include a plurality of apertures and a movable portion configured to selectively move between a first end and a second end according to a gravitational orientation of the plenum chamber.

The apparatus may include an orientation sensor to detect or sense orientation of the plenum chamber, for example by generating a signal indicative of orientation of the plenum chamber, an actuator to adjust opening of the one or more exhaust vents, and/or a controller coupled with the orientation sensor and actuator. The controller may be configured to control adjustment of the one or more exhaust vents in response to detected orientation of the plenum chamber such as in response to the signal indicative of orientation of the plenum chamber. The apparatus may include a sensor adapted to generate a signal indicative of disruption attributable to the exhaust gas, and the one or more exhaust vents may be adjustable to one of a plurality of different venting configurations based on the signal.

In some cases, the one or more exhaust vents may include a first exhaust vent and a second exhaust vent, the first exhaust vent and second exhaust vent located on opposing sides of the plenum chamber to direct exhaust flow in opposing directions. The plenum chamber may be coupled with a mask frame. The plenum chamber may be coupled with headgear. The plenum chamber may form part of a nasal mask. The plenum chamber may form part of a mouth and nose mask. The plenum chamber may form part of a nasal pillow.

The apparatus may further include the respiratory pressure therapy device or flow generator and a respiratory pressure therapy device controller or flow generator controller including a processor. The flow generator controller or respiratory pressure therapy device controller may be configured to control adjustment of an opening of the one or more exhaust vents.

In some cases, an exhaust vent of the one or more exhaust vents may include a swivel having a vent aperture. An exhaust vent of the one or more exhaust vents may include a guide channel having a sliding or rolling movable portion and a plurality of apertures. An exhaust vent of the one or more exhaust vents may include a set of movable leaves with an adjustable aperture central to the set of leaves. The one or more vents may be adjustable to increase an exhaust area of a first vent and decrease an exhaust area of a second vent responsive to an orientation of the plenum chamber. In some cases, a controller may be configured to adjust the one or more vents based on a detected orientation of the plenum chamber to increase an exhaust area of a first vent and decrease an exhaust area of a second vent.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including.

5.1 Treatment Systems

5.2 Therapy 5.2.1 Respiratory System

Figure 2A:
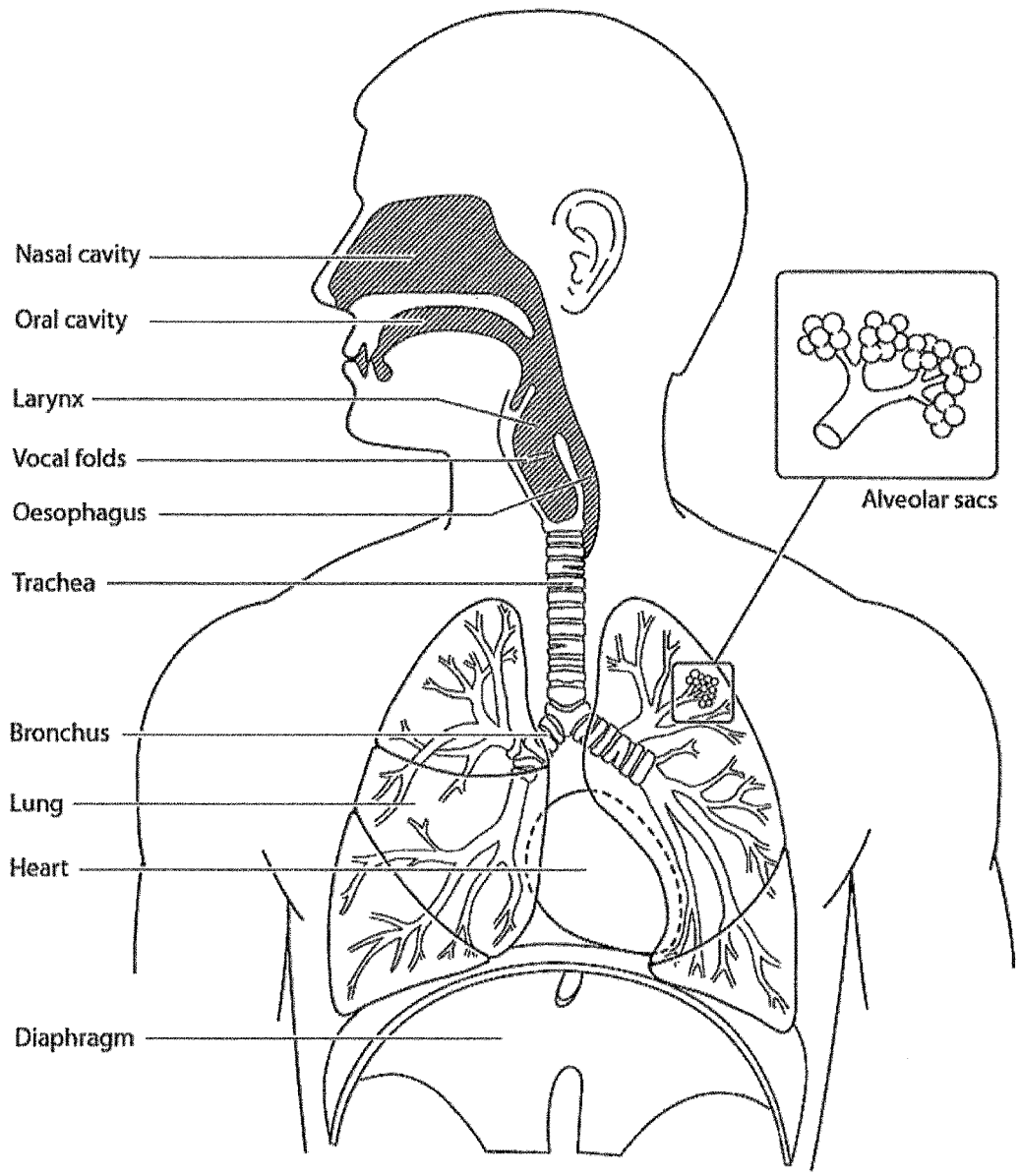

FIG. 2a shows an overview of a human respiratory system including the nasal and oral cavities, the larynx, vocal folds, oesophagus, trachea, bronchus, lung, alveolar sacs, heart and diaphragm.

Figure 2B:
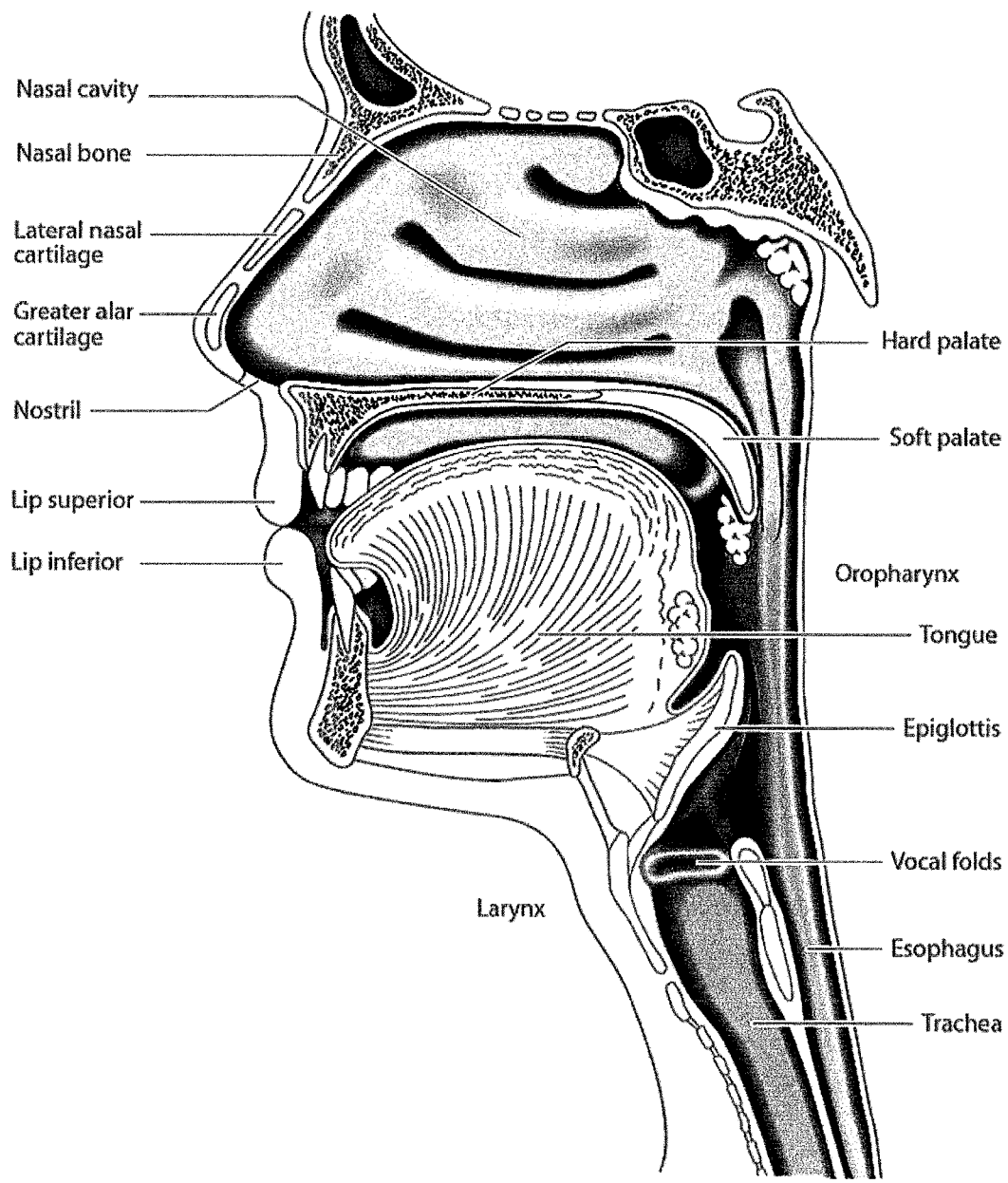

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

5.2.2 Facial Anatomy

Figure 2C:
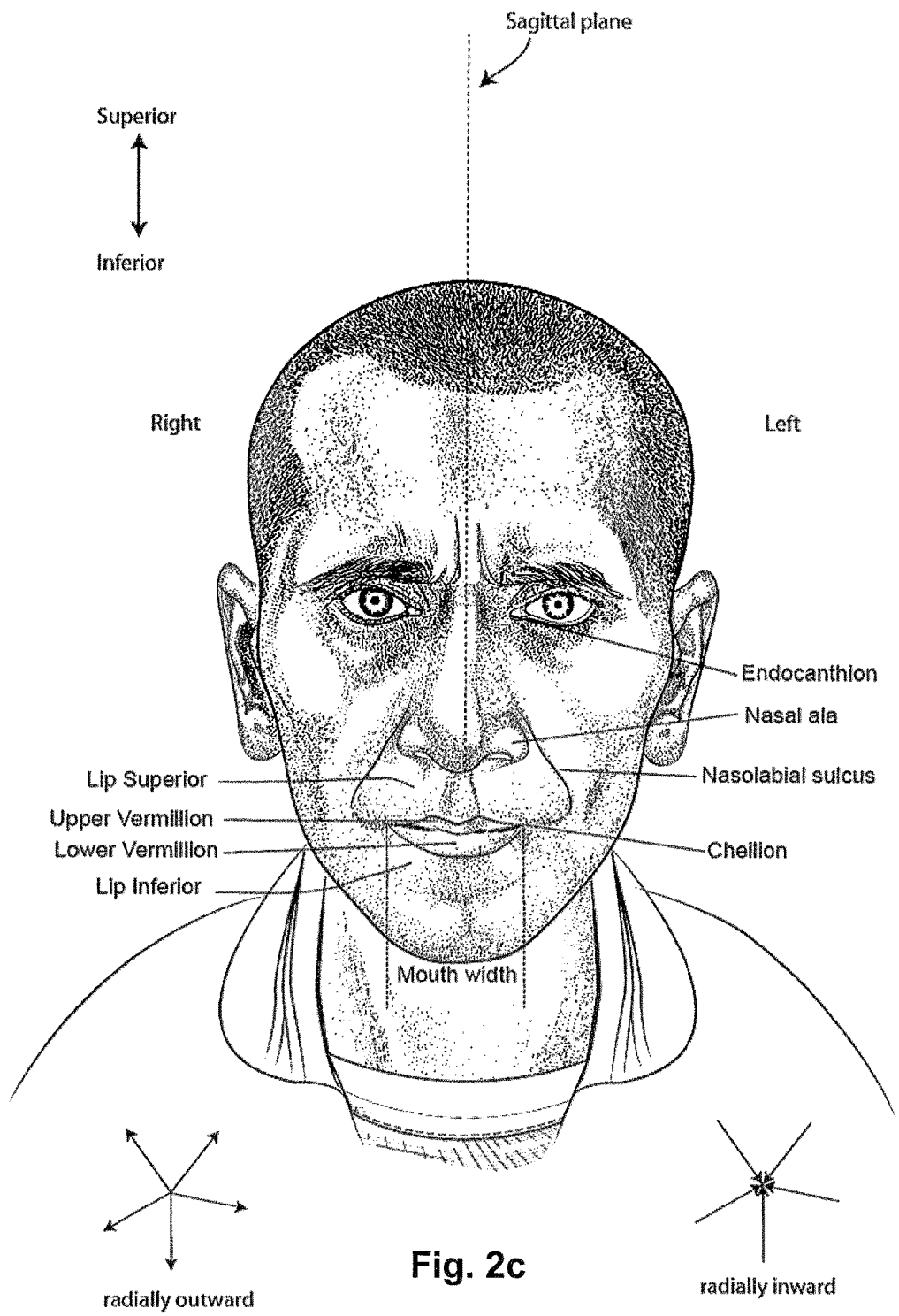

FIG. 2c is a front view of a face with several features of surface anatomy identified including the lip superior, upper vermillion, lower vermillion, lip inferior, mouth width, endocanthion, a nasal ala, nasolabial sulcus and cheilion.

5.3 Patient Interface

Figure 3A:
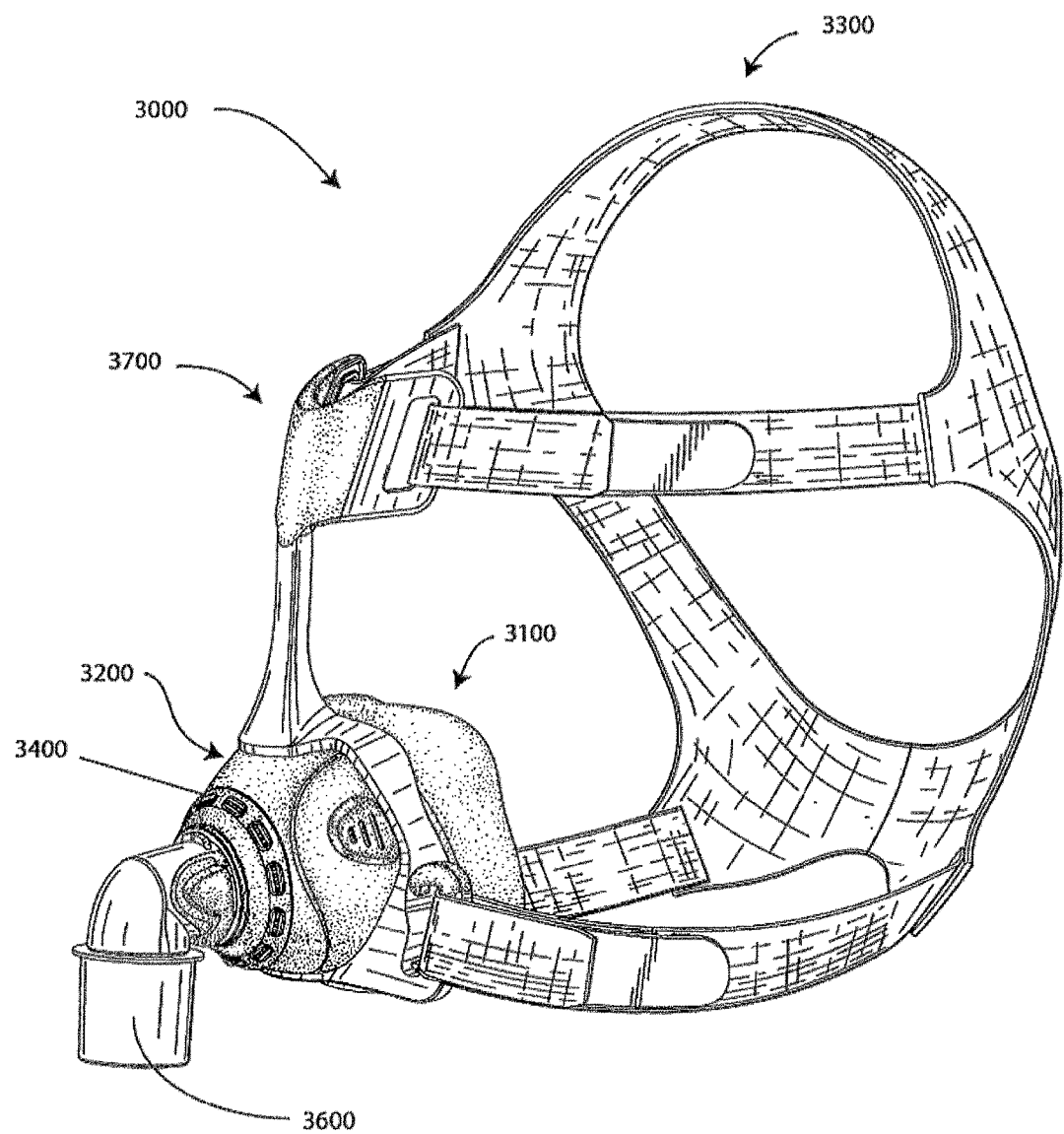

FIG. 3a shows an example of a patient interface known in the prior art.

5.4 Respiratory Pressure Therapy (RPT) Device

Figure 4A:
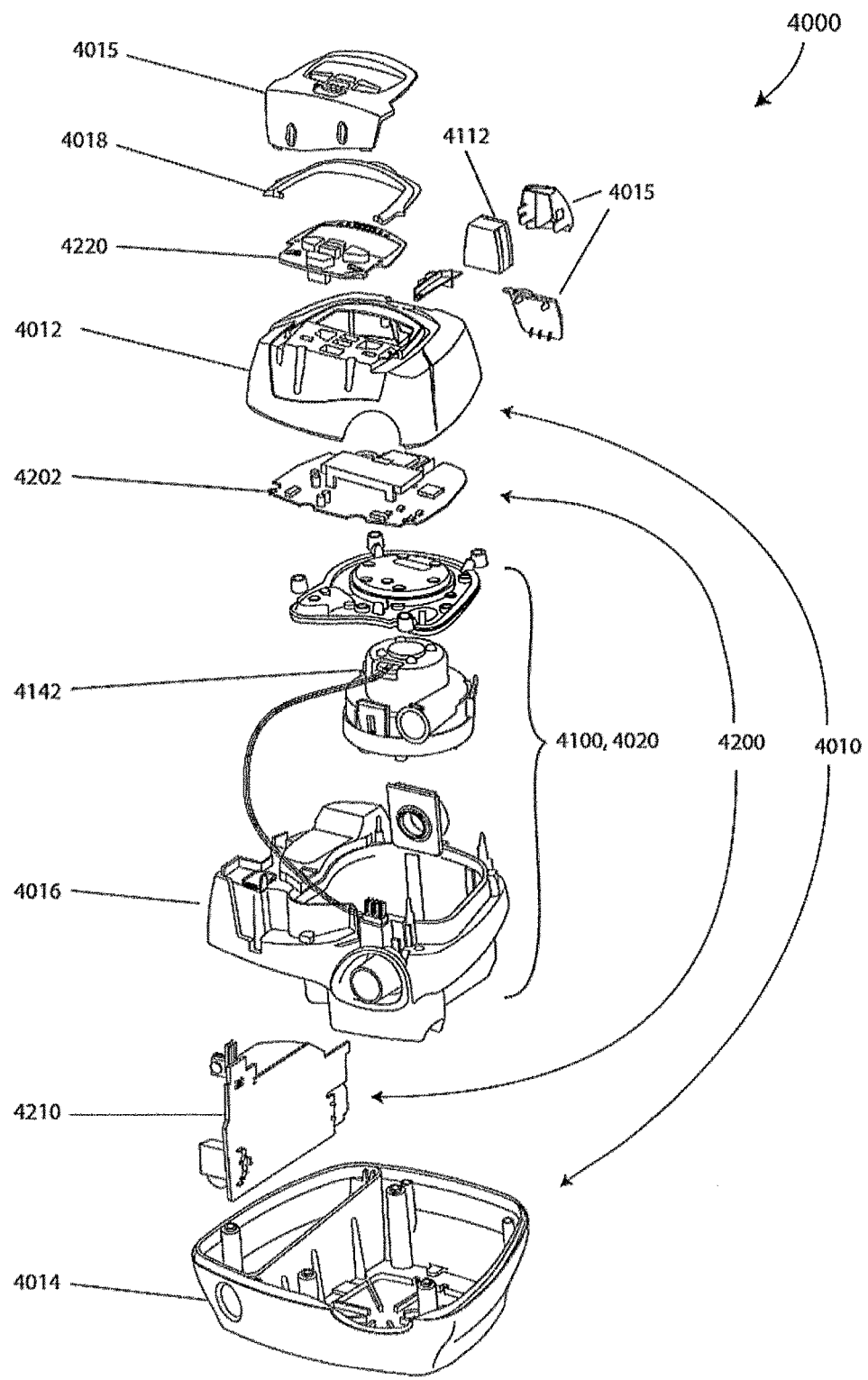

FIG. 4a shows a RPT device in accordance with one form of the present technology.

Figure 4B:
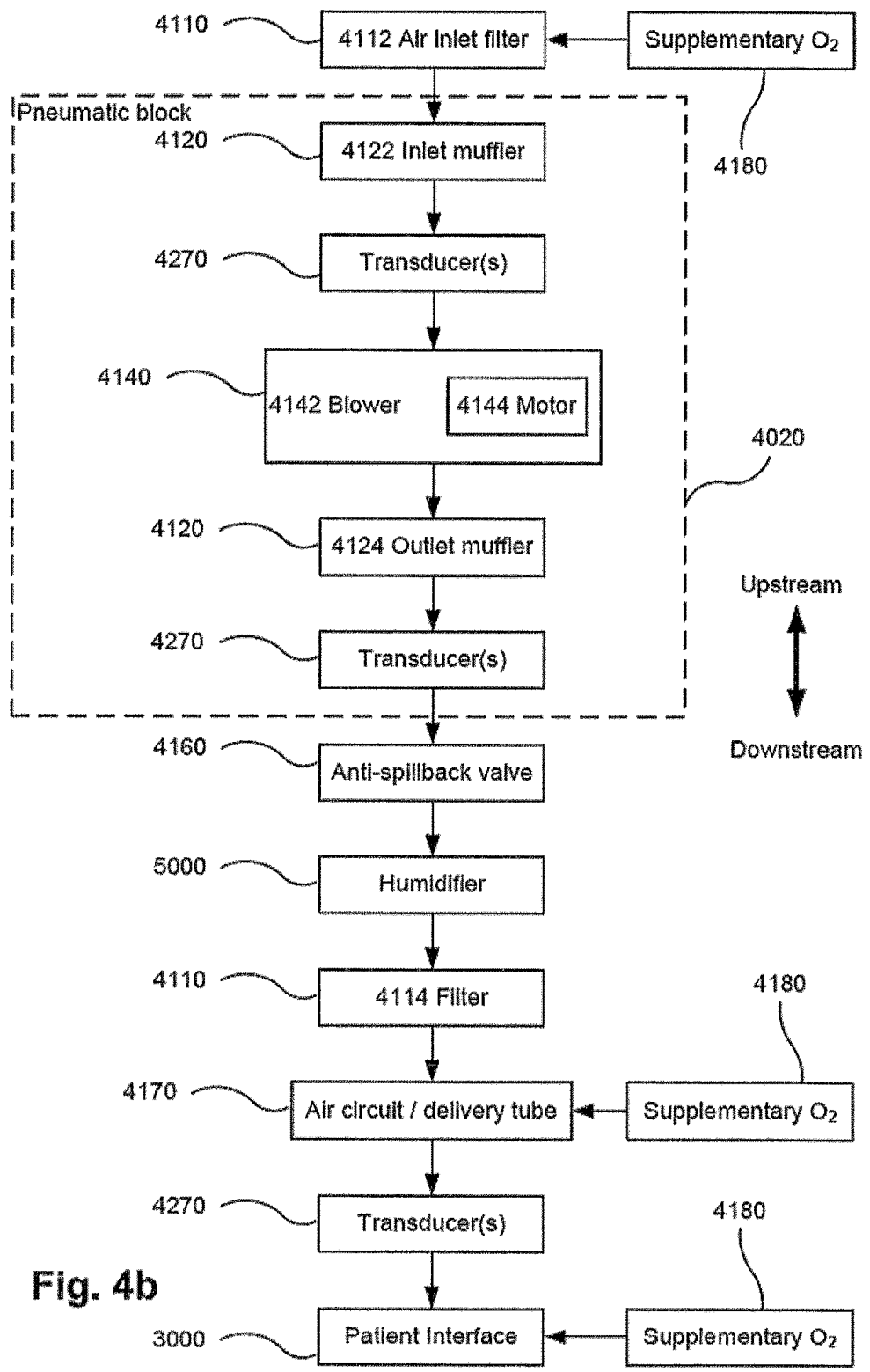

FIG. 4b shows a schematic diagram of the pneumatic circuit of a RPT device in accordance with one form of the present technology. The directions of upstream and downstream are indicated.

Figure 4C:
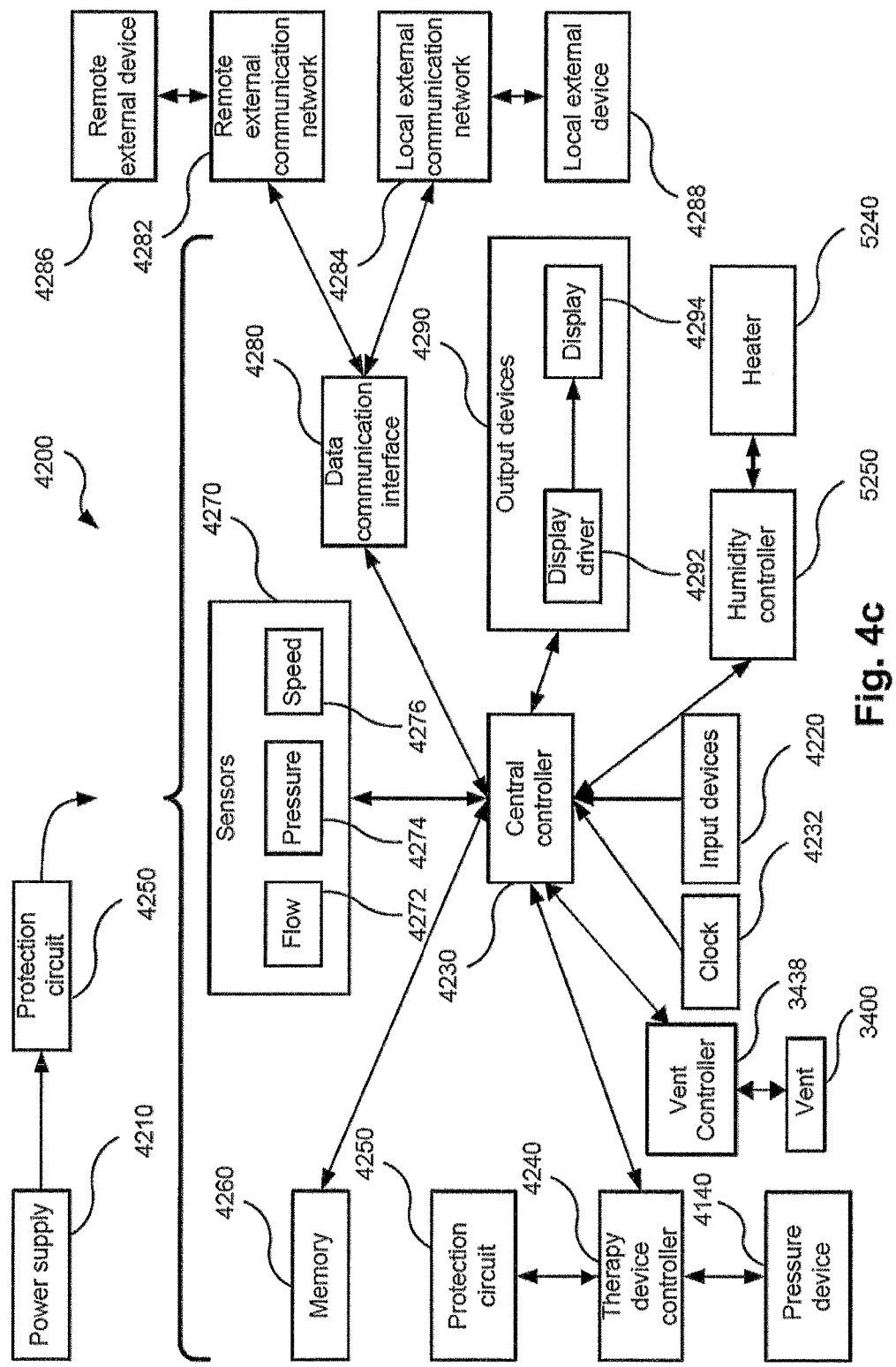

FIG. 4c shows a schematic diagram of the electrical components of a RPT device in accordance with one aspect of the present technology.

5.5 Humidifier

Figure 5A:
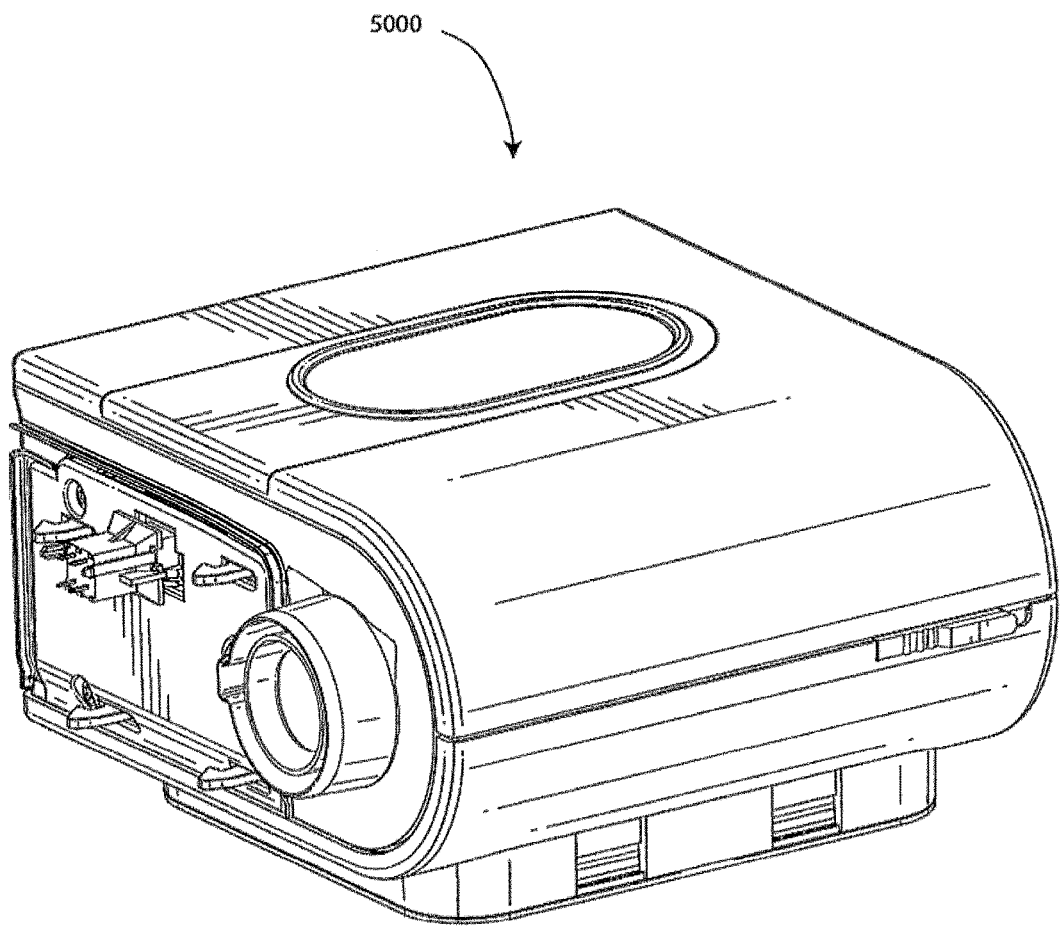

FIG. 5a shows a humidifier in accordance with one aspect of the present technology.

5.6 Breathing Waveforms

FIG. 6a shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

5.7 Gas Washout Vent Arrangements

Figure 7:
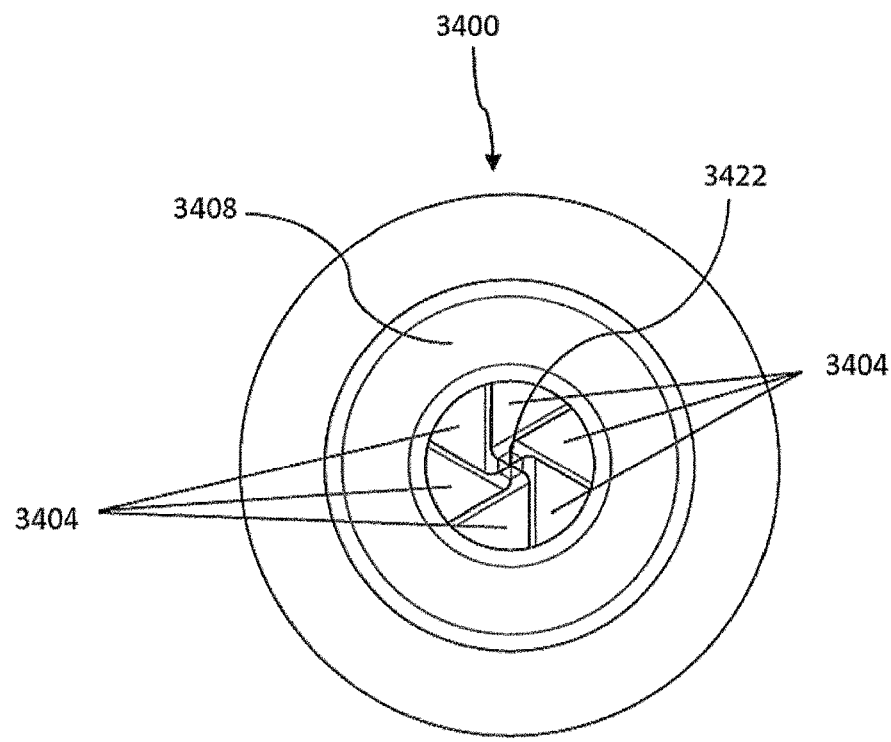
Figure 8:
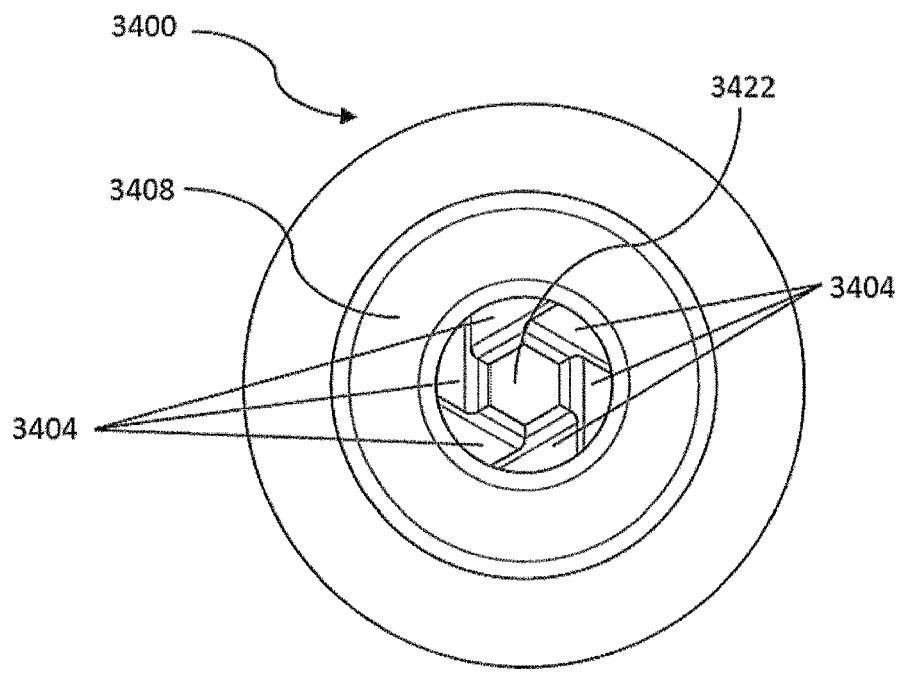

FIG. 7-8 show front views of one form of a vent according to the current technology. FIG. 7 shows a configuration of the vent where the adjustable vent aperture 3422 is closed, and FIG. 8 shows another configuration where the adjustable vent aperture 3422 has been enlarged.

Figure 9:
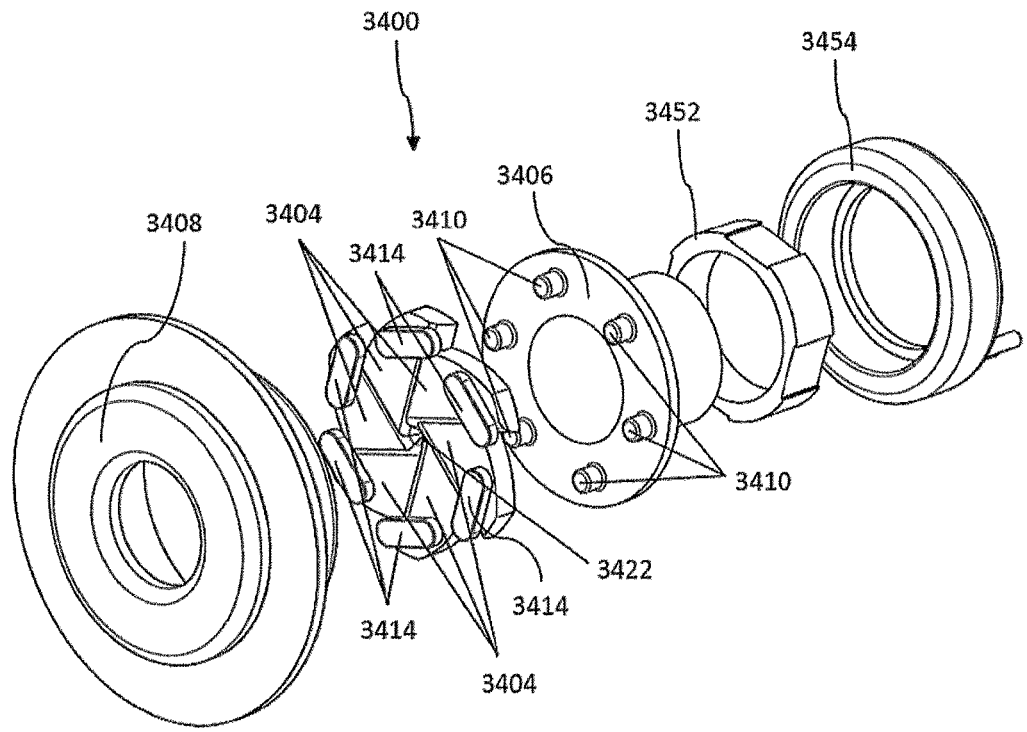
Figure 10:
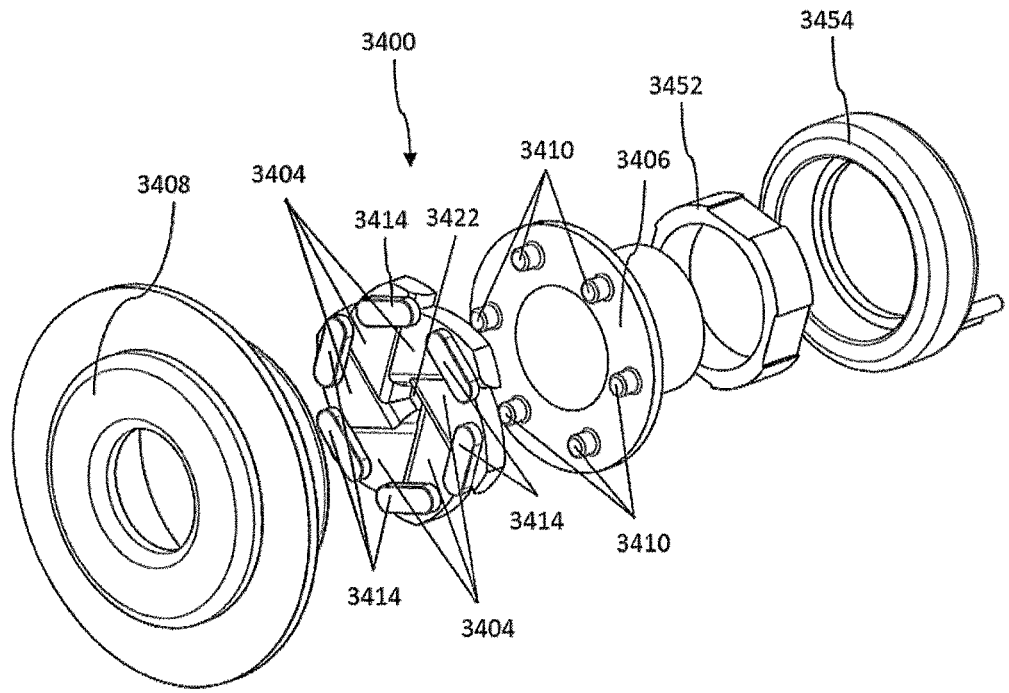
Figure 11:
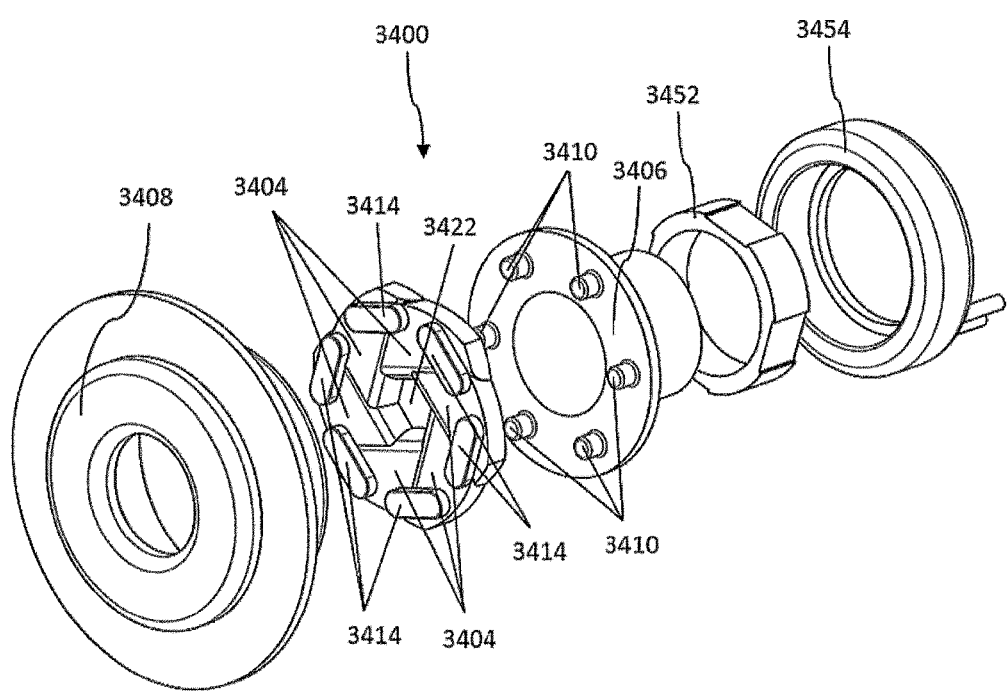

FIG. 9-11 show exploded perspective views of one form of a vent according to the current technology. FIG. 9 shows a configuration of the vent where the vent aperture 3422 is closed, FIG. 10 shows another configuration where the vent aperture 3422 has been enlarged and FIG. 11 shows another configuration where the vent aperture 3422 has been enlarged further.

Figure 12A:
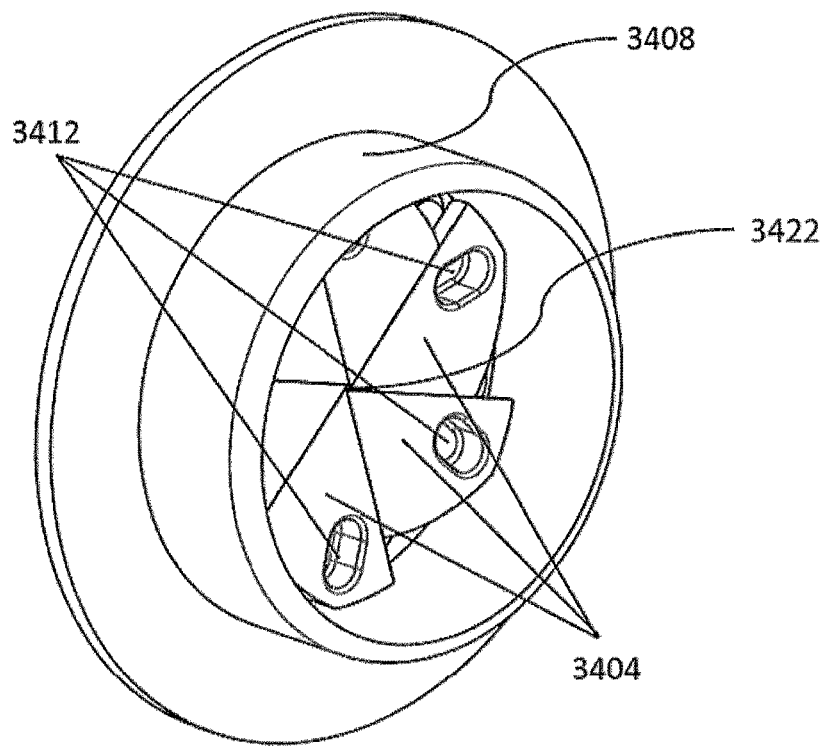
Figure 12B:
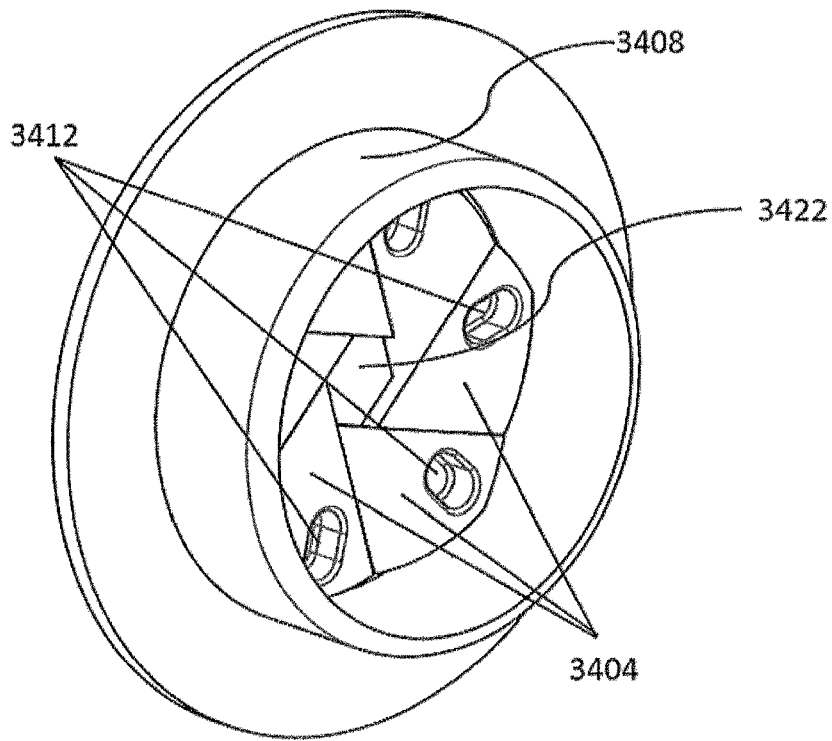

FIG. 12a-12b show rear perspective views of one form of a vent according to the current technology. FIG. 12a shows a configuration of the vent where the vent aperture 3422 is closed, and FIG. 12b shows another configuration where the vent aperture 3422 has been enlarged.

Figure 13:
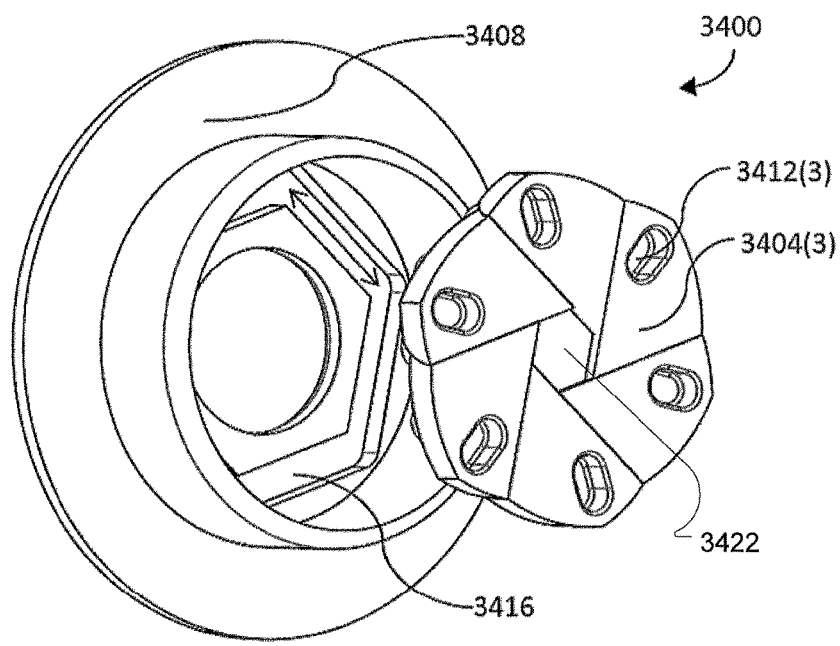

FIG. 13 shows an exploded rear perspective view of some components of a vent according to the current technology.

Figure 14A:
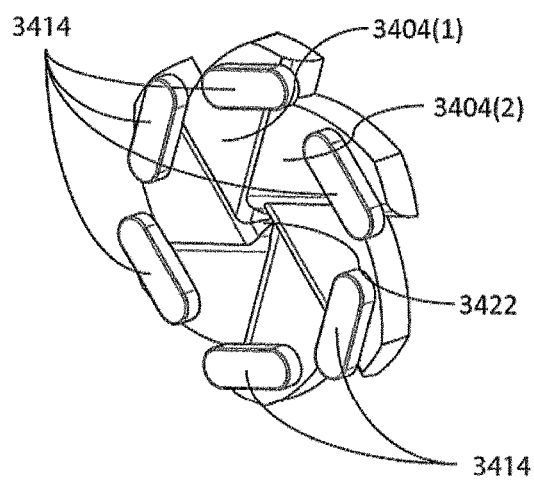
Figure 14B:
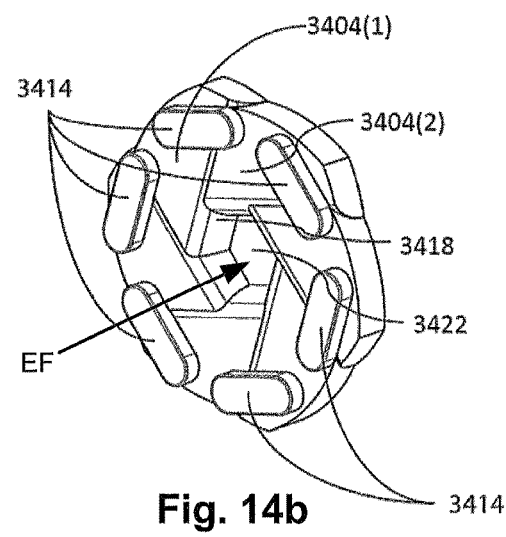

FIG. 14a-14b show front perspective views of components of a vent according to the current technology, showing the leaves 3404. FIG. 14a shows a configuration of the leaves 3404 where the vent aperture 3422 is partially closed, and FIG. 14b shows another configuration where the vent aperture 3422 has been enlarged.

Figure 15:
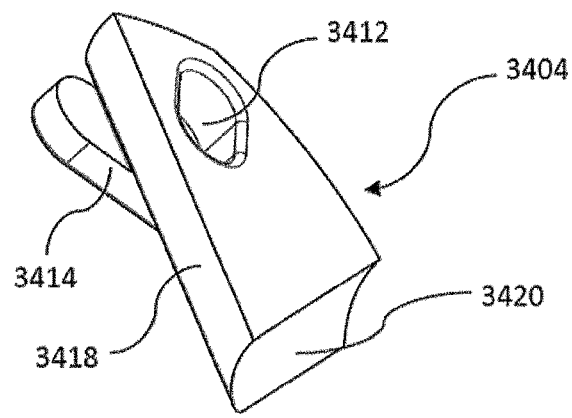

FIG. 15 shows a rear perspective view of one form of a leaf 3404 according to the current technology.

Figure 16:
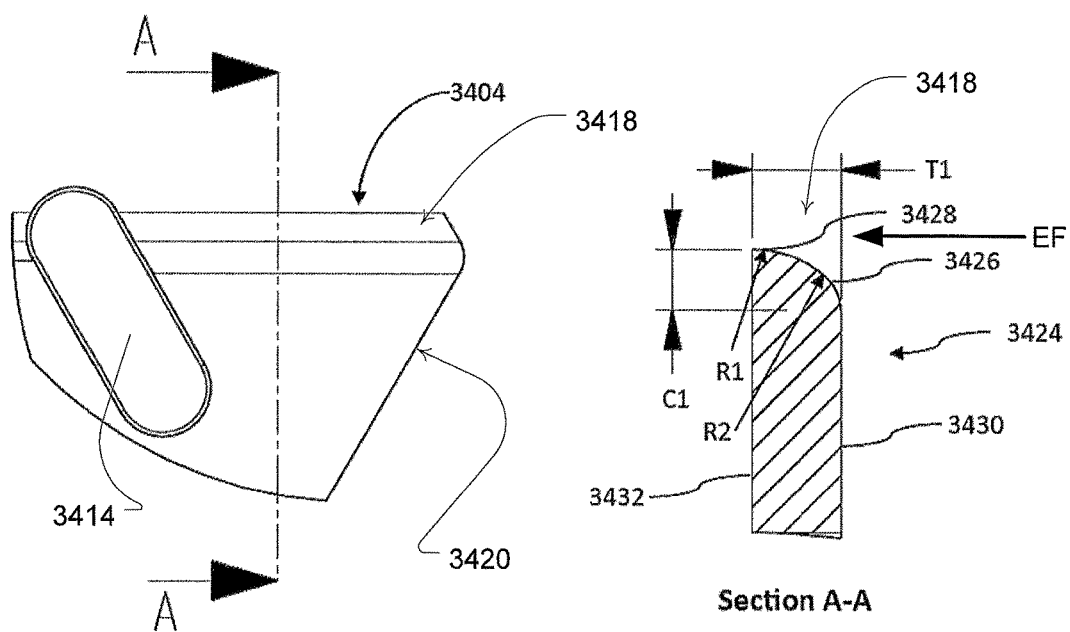

FIG. 16 shows a front view of one form of a leaf 3404 according to the current technology, with a cross-sectional view of the leaf 3404 taken along line A-A.

Figure 17:
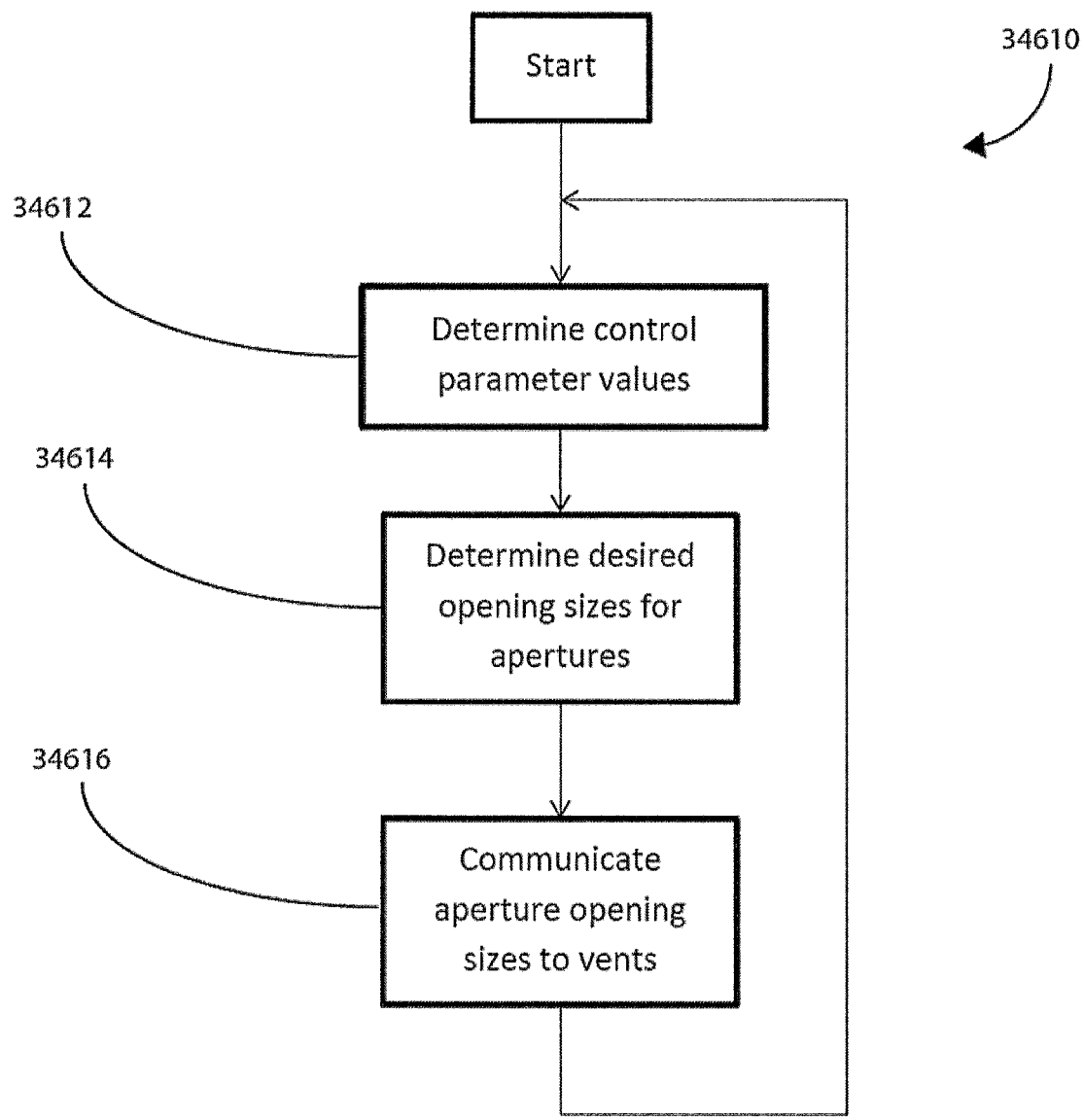

FIG. 17 shows a flow chart of one form of a vent aperture size control methodology of the current technology.

Figure 18:
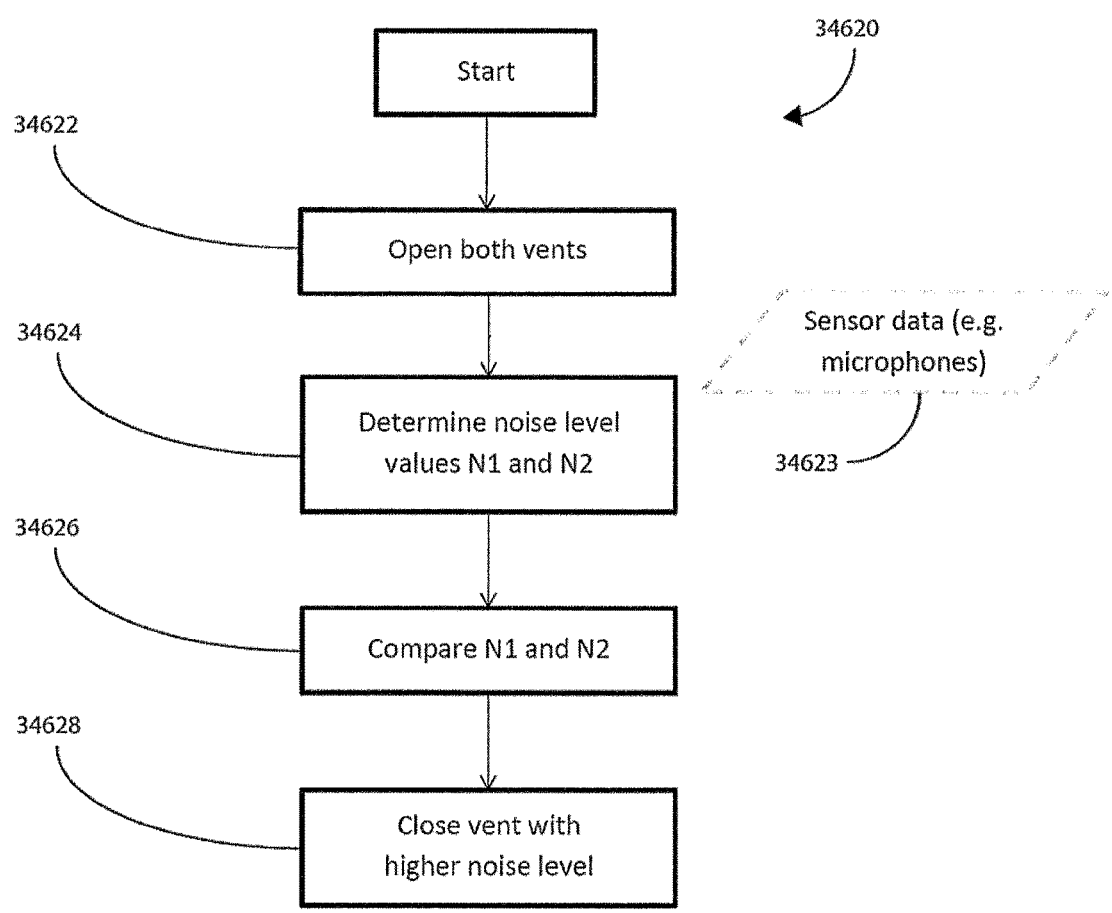

FIG. 18 shows a flow chart of one form of a vent aperture size control methodology of the current technology wherein a plurality of vents are used as well as a plurality of noise levels.

Figure 19:
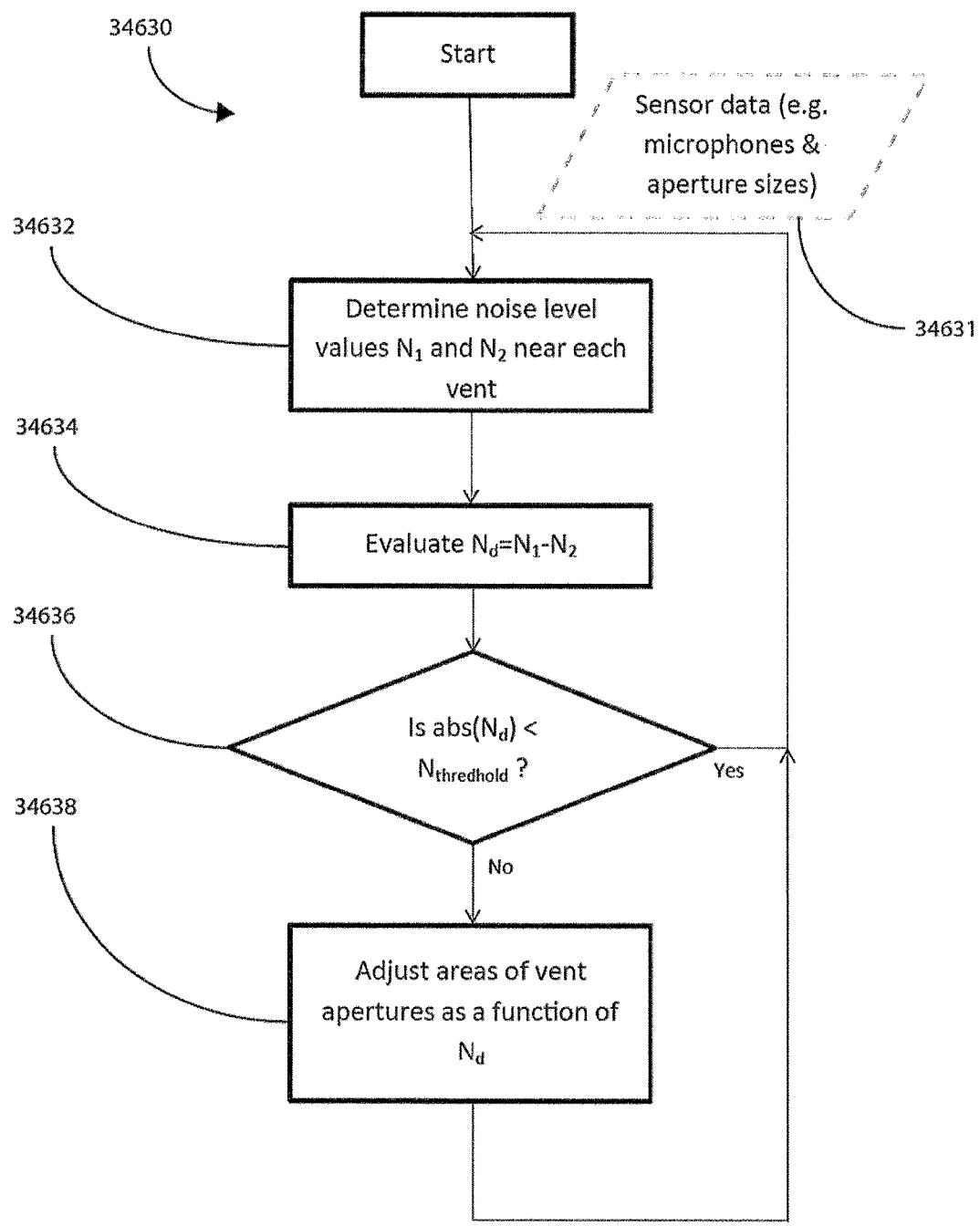

FIG. 19 shows a flow chart of one form of a vent aperture size control methodology of the current technology wherein a plurality of vents are used as well as a plurality of noise levels and a threshold noise level.

Figure 20:
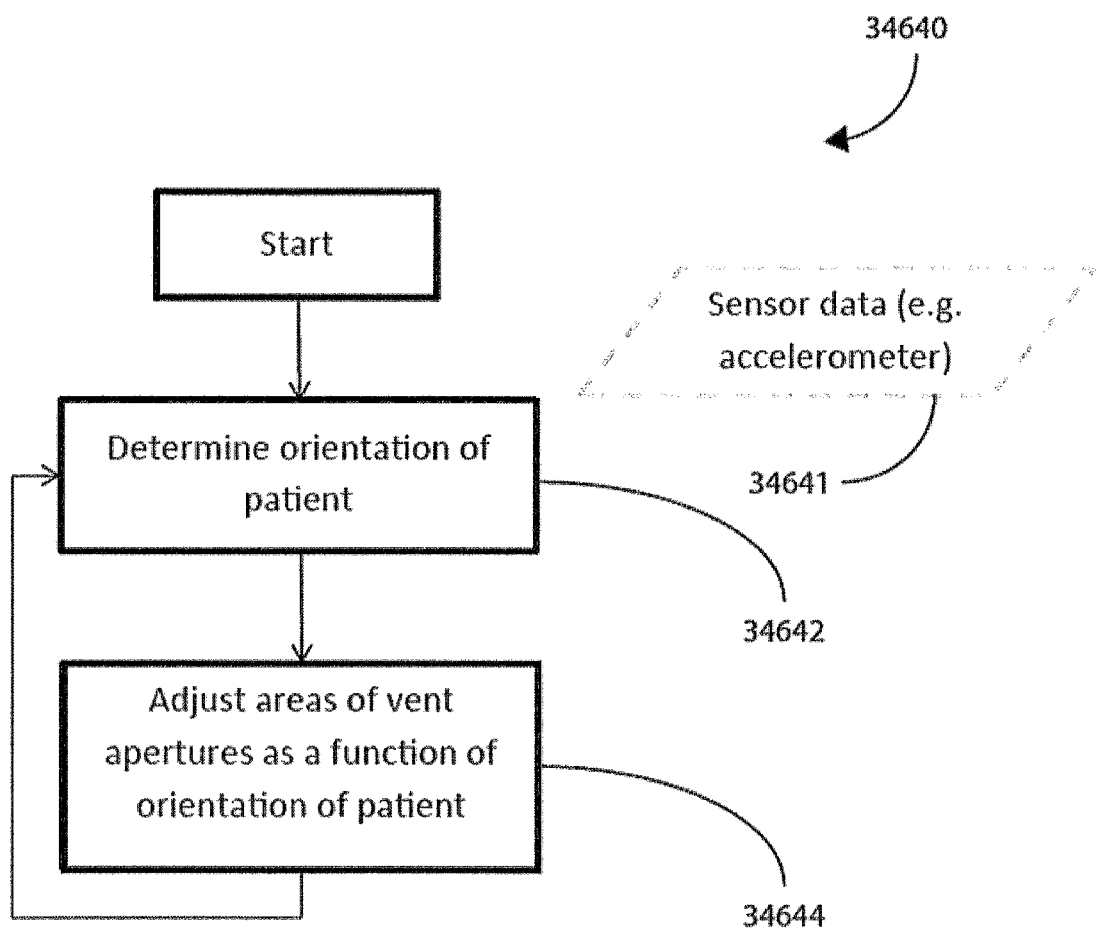

FIG. 20 shows a flow chart of one form of a vent aperture size control methodology of the current technology wherein the orientation of the patient is used.

Figure 21:
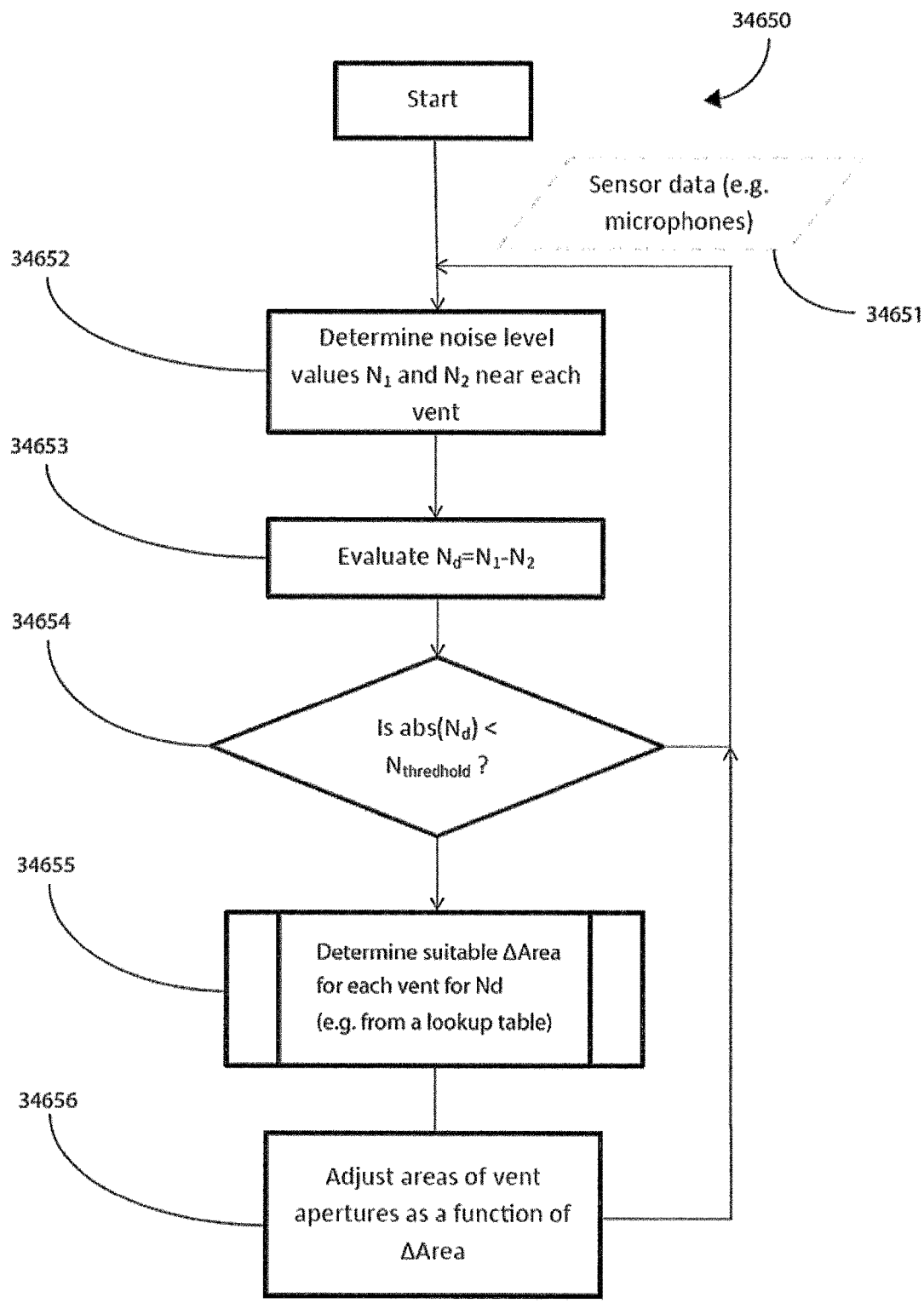

FIG. 21 shows a flow chart of one form of a vent aperture size control methodology of the current technology wherein a plurality of vents are used as well as a plurality of noise levels, a threshold noise level and a lookup table.

Figure 22:
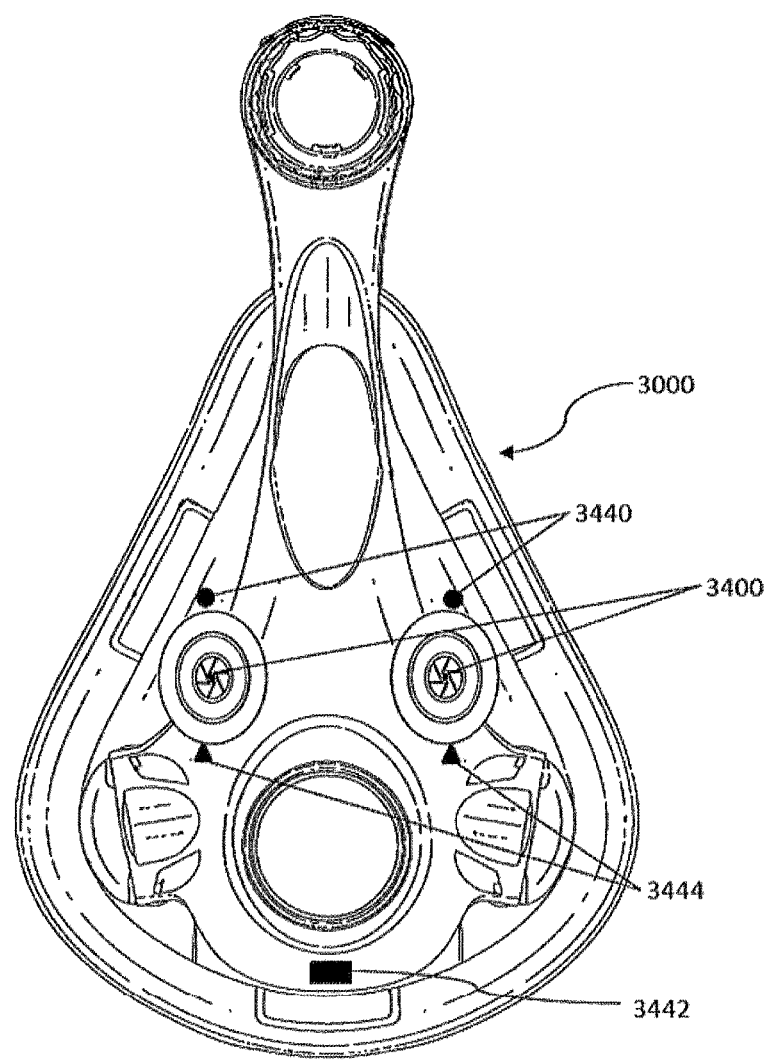

FIG. 22 shows a front view of one form of a patient interface 3000 according to the current technology, including a plurality of vents 3400 and sensors such as microphones 3440, proximity sensors 3444 and accelerometer(s) 3442.

Figure 23A:
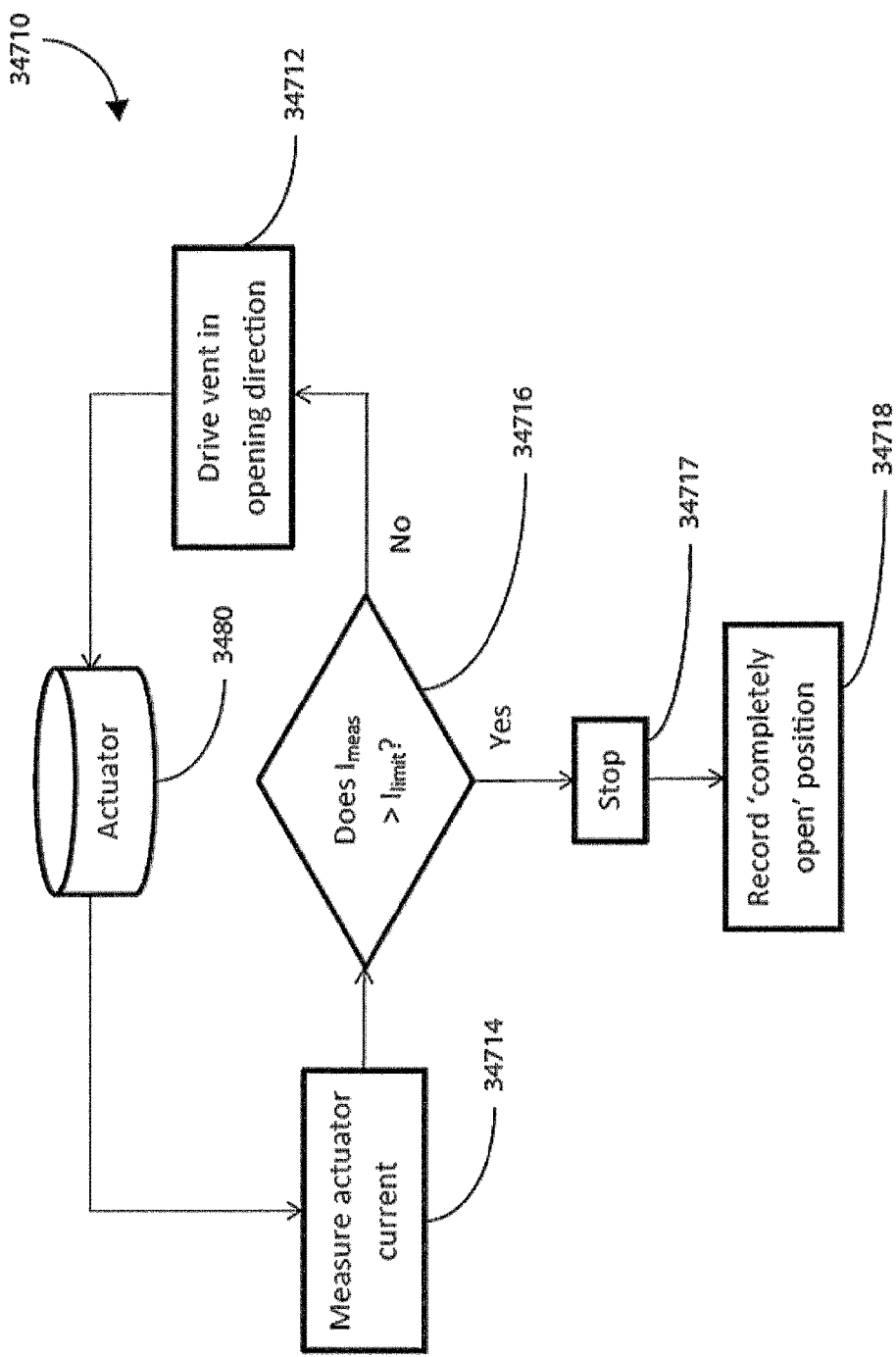

FIG. 23a shows a flow chart of one form of a vent actuator calibration methodology of the current technology wherein the 'completely open' position is recorded.

Figure 23B:
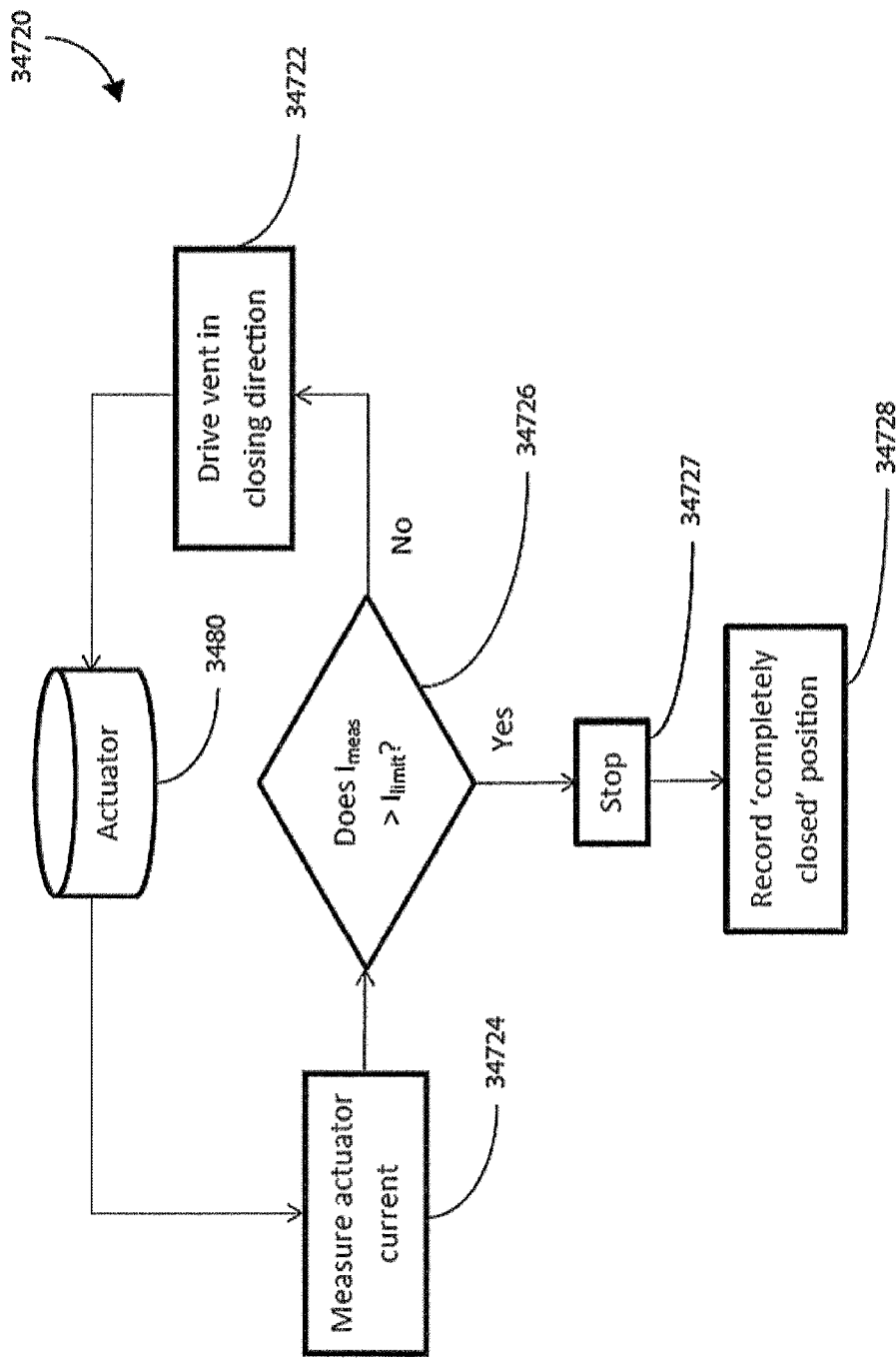

FIG. 23b shows a flow chart of one form of a vent actuator calibration methodology of the current technology wherein the 'completely closed' position is recorded.

Figure 24:
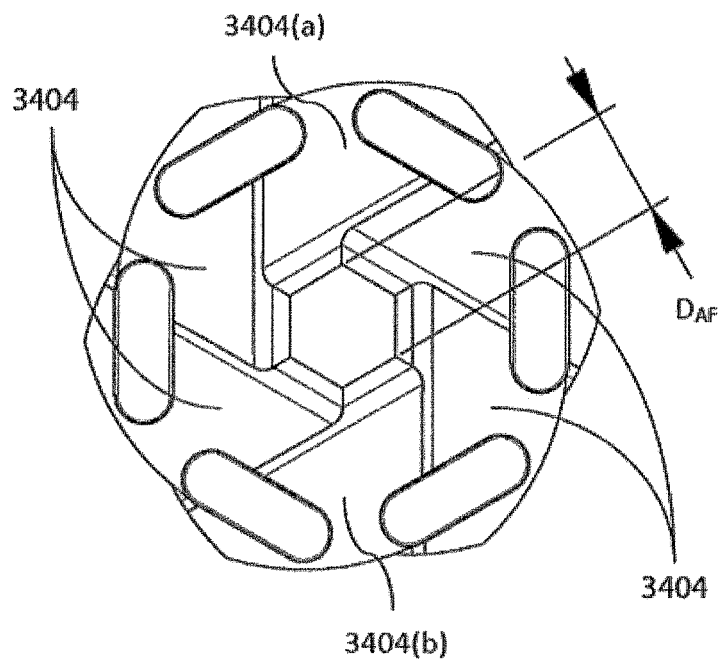

FIG. 24 shows a front view of one form of some components of a vent according to the current technology, particularly showing the leaves 3404, such as leaves 3404(*a*) and 3404(*b*).

Figure 25:
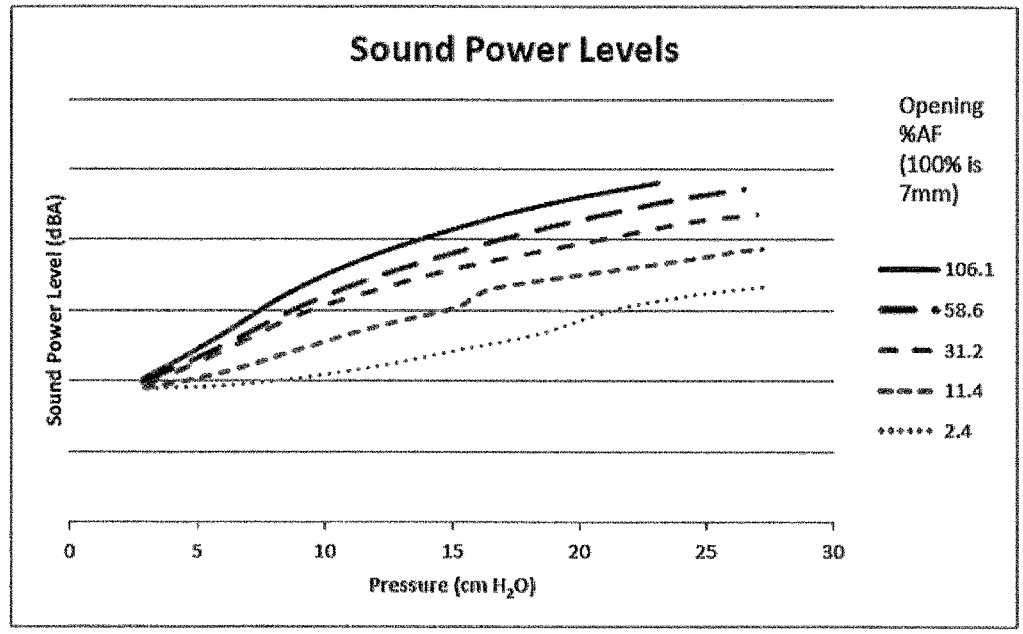

FIG. 25 is a graph of sound power levels according to one form of a vent according to the current technology, showing the comparative sound power levels according to various therapy pressures and opening sizes.

Figure 26A:
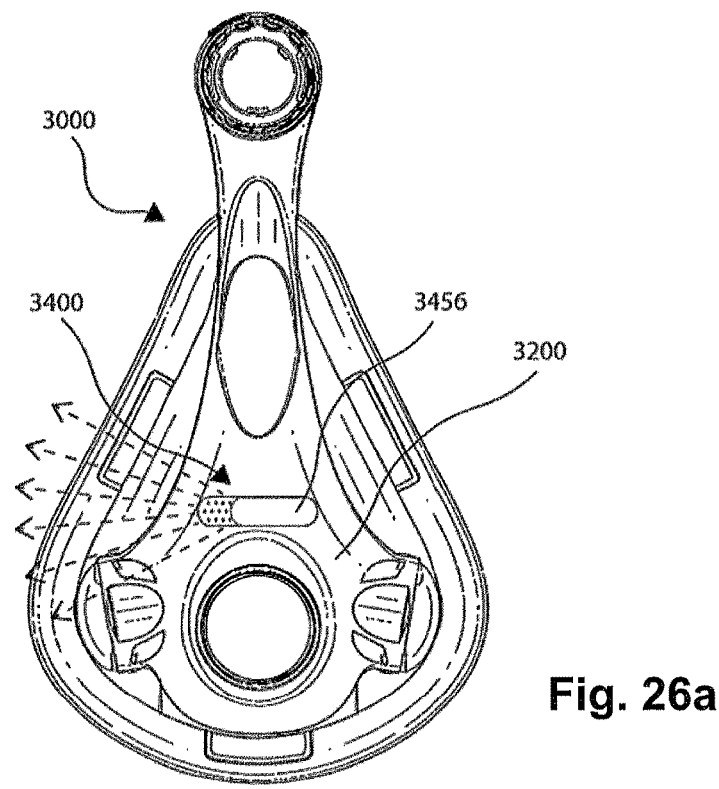
Figure 26B:
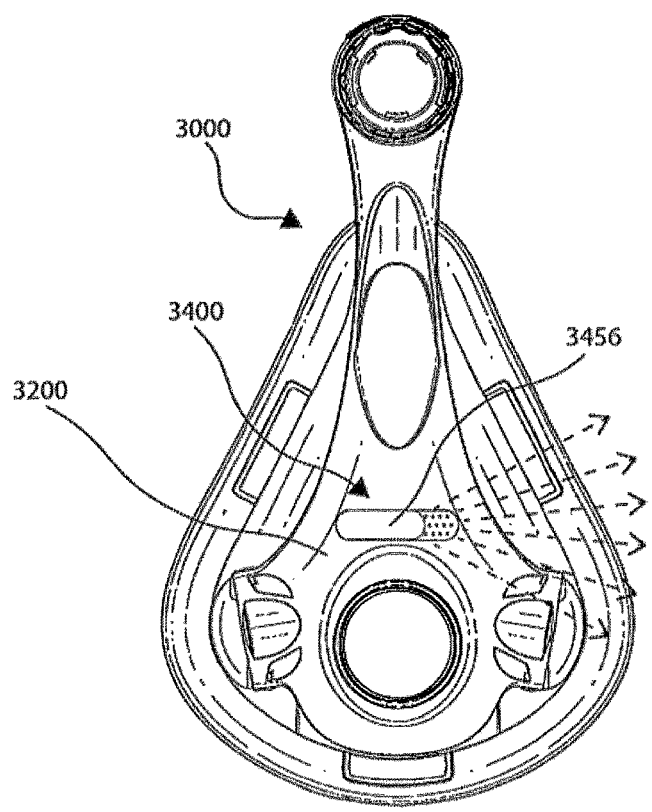

FIG. 26*a*-26*b* show front views of one form of a patient interface 3000 according to the current technology, including a vent 3400 with a movable portion 3456.

Figure 27A:
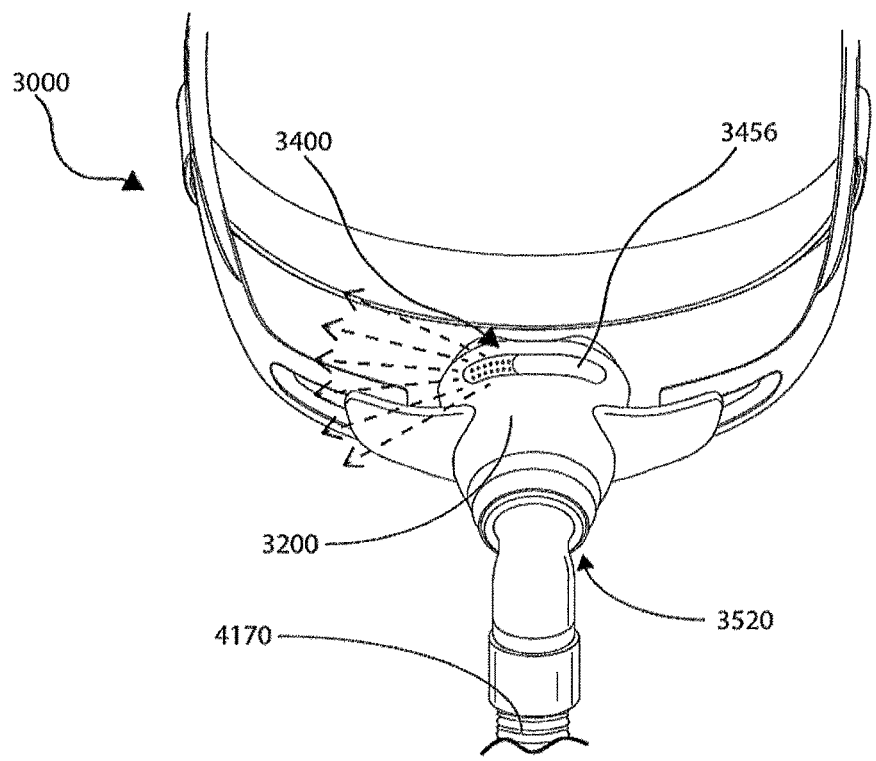
Figure 27B:
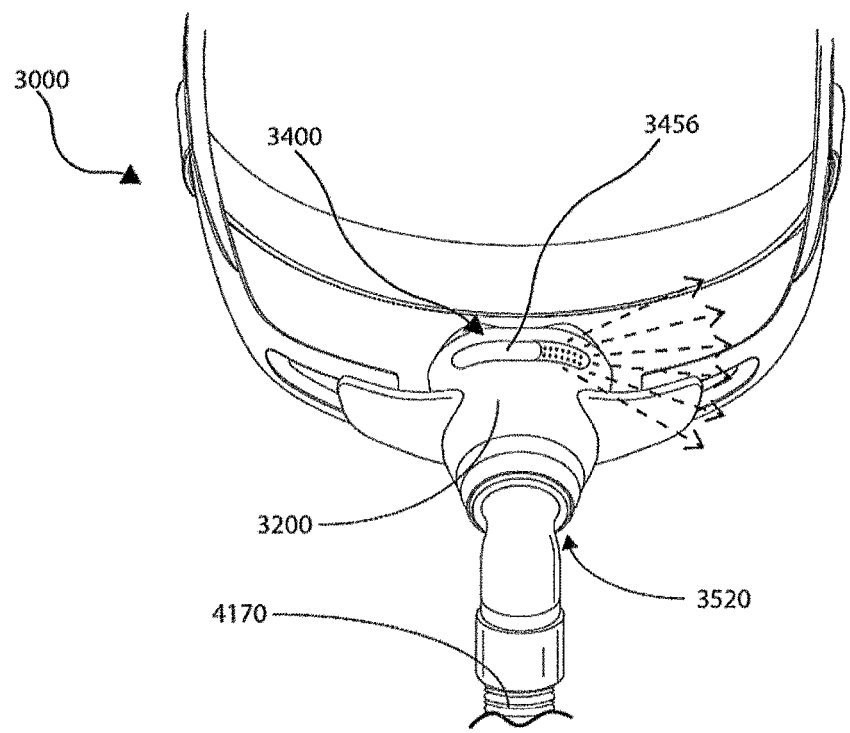

FIG. 27*a*-27*b* show front views of another form of a patient interface 3000 according to the current technology, including a vent 3400 with a movable portion 3456.

Figure 28A:
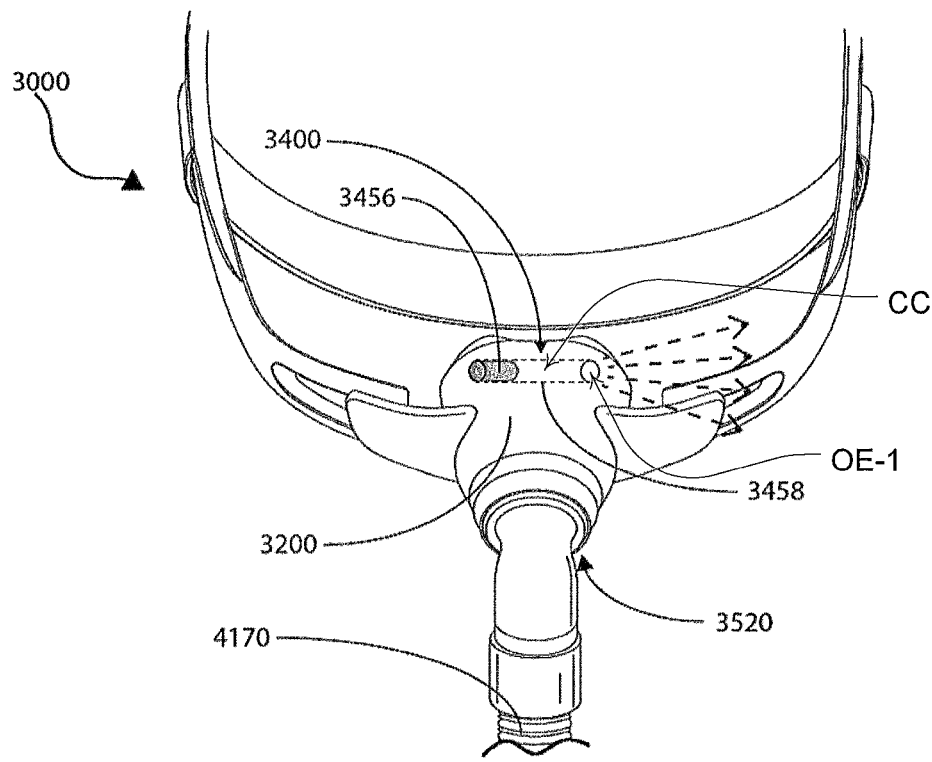
Figure 28B:
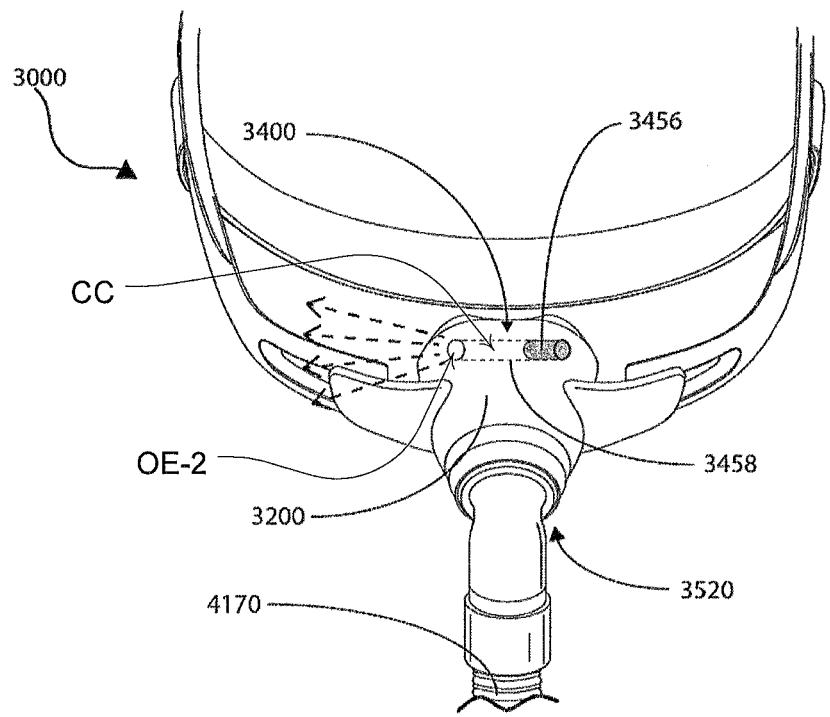

FIG. 28*a*-28*b* show front views of a yet another form of a patient interface 3000 according to the current technology, including a vent 3400 with a movable portion 3456 which is adapted to move, such as according to gravity, in a guiding portion 3458.

Figure 29:
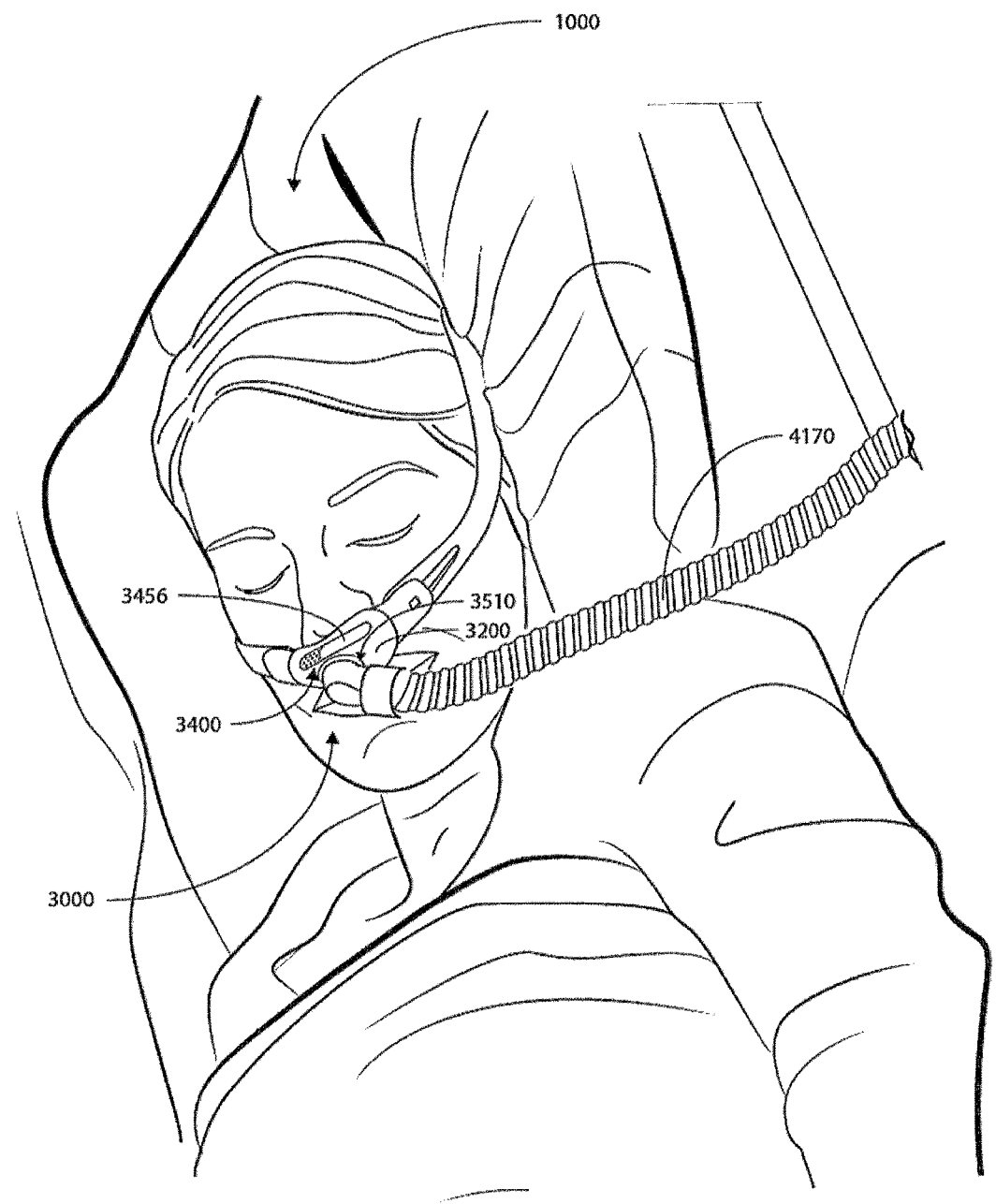

FIG. 29 shows a patient 1000 lying on a bed wearing a patient interface 3000 according to an aspect of the present technology, wherein patient interface 3000 includes a movable portion 3456.

Figure 30A:
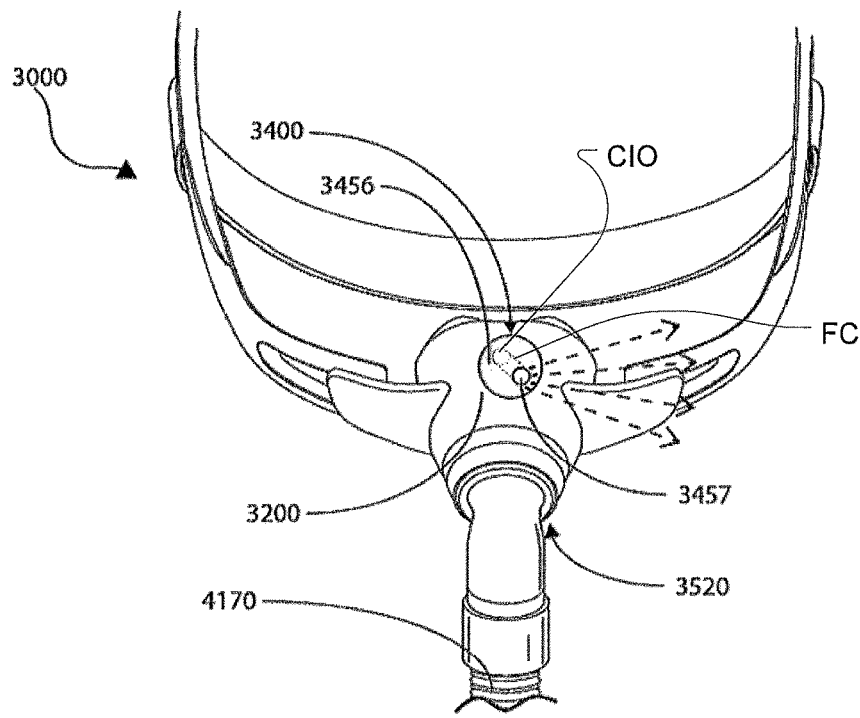
Figure 30B:
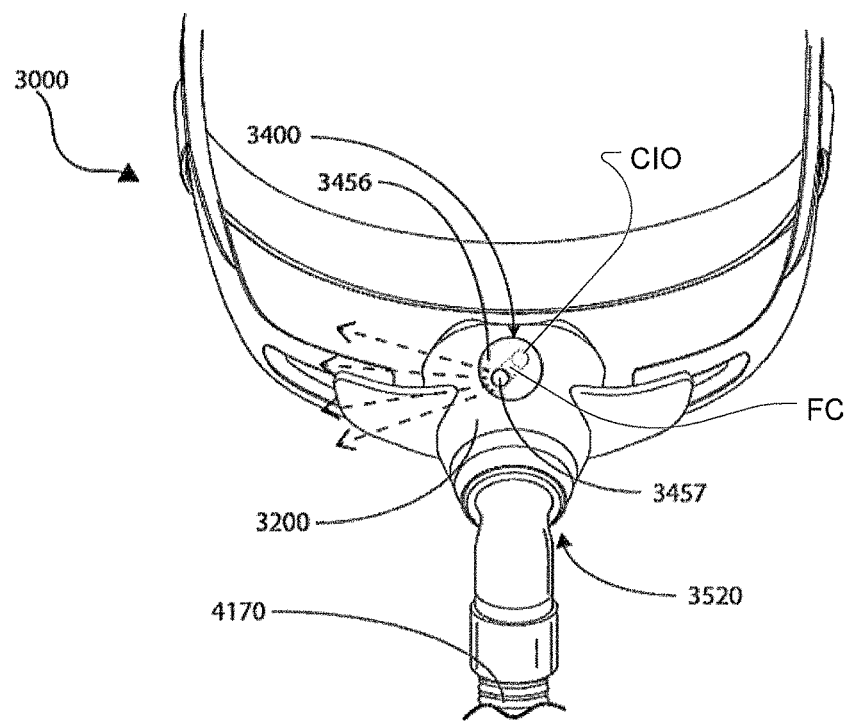

FIGS. 30*a*-30*b* show front views of a yet another form of a patient interface 3000 according to the current technology, including a vent 3400 with a movable portion 3456, such as one which is adapted to rotate to vary the direction of the aperture 3457.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

6.1 Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

6.2 Therapy

In one form, the present technology comprises a method for treating a respiratory disorder comprising the step of applying positive pressure to the entrance of the airways of a patient 1000.

6.2.1 Nasal CPAP for OSA

In one form, the present technology comprises a method of treating Obstructive Sleep Apnea in a patient by applying nasal continuous positive airway pressure to the patient.

6.3 Patient Interface 3000

A non-invasive patient interface 3000 in accordance with one aspect of the present technology comprises the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

6.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter 3210 of the plenum chamber 3200. Support flange may be relatively thicker than the sealing flange. The support flange is disposed between the sealing flange and the marginal edge of the plenum chamber 3200, and extends at least part of the way around the perimeter 3210. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

6.3.2 Plenum Chamber 3200

Preferably the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Figure 1A:
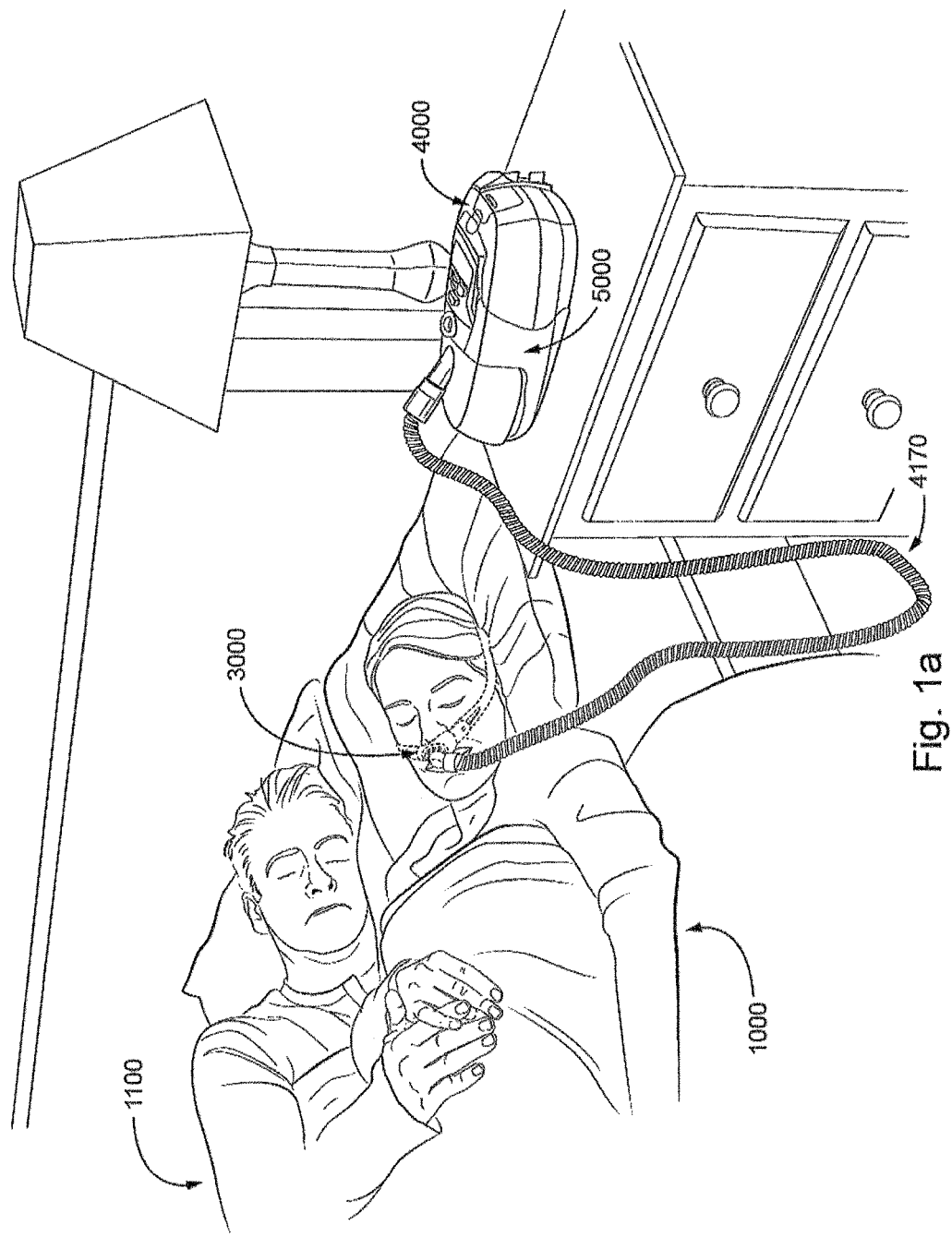
FIG. 1a shows a system in accordance with the present technology. A patient 1000 wearing a patient interface 3000, in the form of nasal pillows, receives a supply of air at positive pressure from a RPT device 4000. Air from the RPT device is humidified in a humidifier 5000, and passes along an air circuit 4170 to the patient 1000.
Figure 1B:
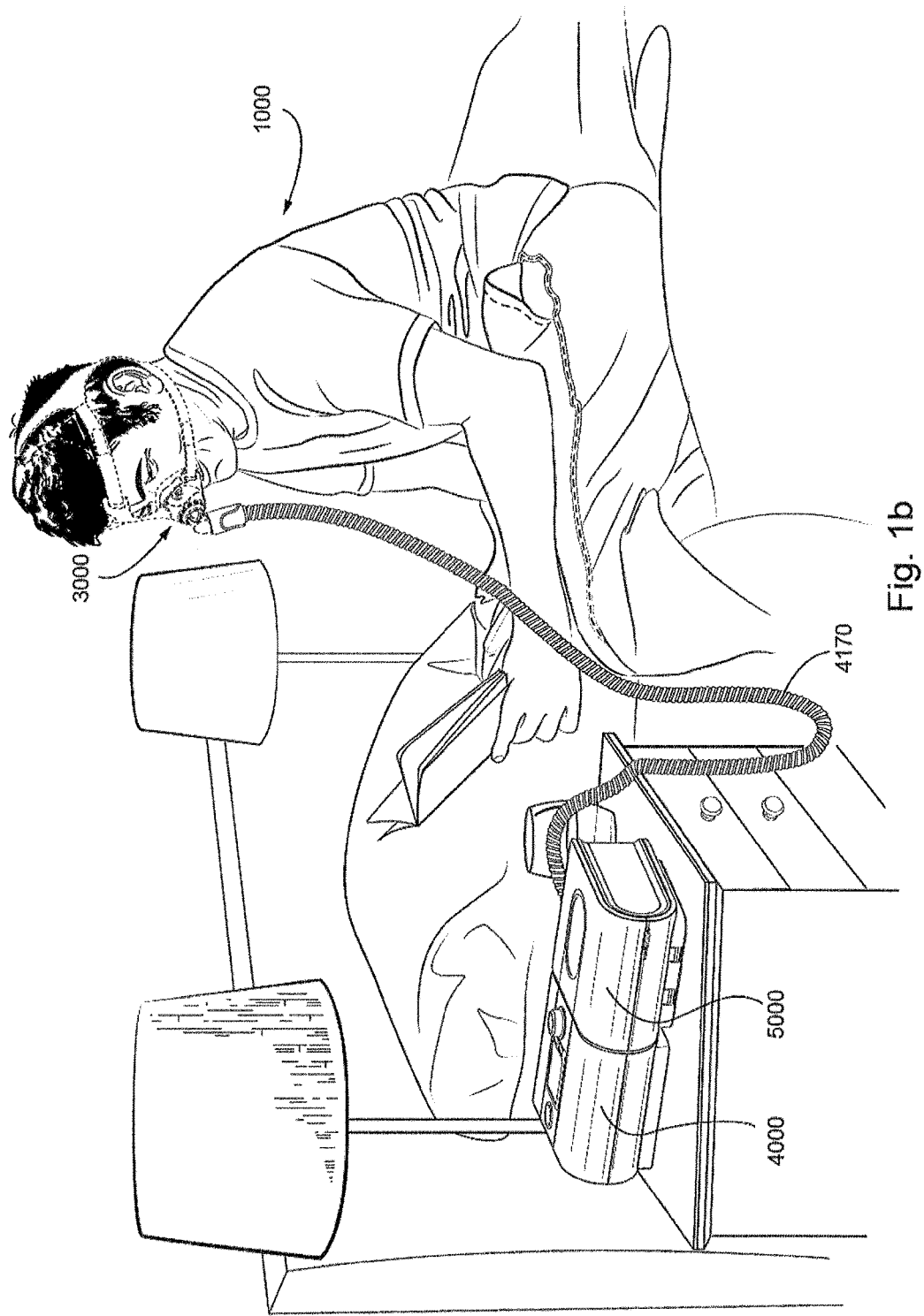
FIG. 1b shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
Figure 1C:
FIG. 1c shows a system including a patient 1000 wearing a patient interface 3000, in the form of a full-face mask, receives a supply of air at positive pressure from a RPT device. Air from the RPT device is humidified in a humidifier 5000, and passes along an air circuit 4170 to the patient 1000.

In one form, the plenum chamber 3200 may surround and/or be in fluid communication with the nares of the patient where the plenum chamber 3200 is a part of a nasal mask (e.g. shown in FIFG. 1*b*). In another form, the plenum chamber 3200 may surround and/or be in fluid communication with the flares and the mouth of the patient where the plenum chamber 3200 is a part of a full-face mask (e.g., shown in FIG. 1*c*). In yet another form, the plenum chamber 3200 may engage and/or be in fluid communication with one or more of the nares of the patient where the plenum chamber 3200 is a part of nasal pillows (e.g., shown in FIG. 29).

6.3.3 Positioning and Stabilising Structure 3300

Preferably the seal-forming structure 3100 of the patient interface 3000 of the present technology is held in sealing position in use by the positioning and stabilising structure 3300.

6.3.4 Vent 3400

In one form, the patient interface 3000 includes a vent 3400 constructed and arranged to allow for the washout of exhaled carbon dioxide or any other exhaust gas from the patient interface 3000.

One form of vent 3400 known in the prior art comprises a plurality of holes, for example, about 20 to about 80 holes, or about 40 to about 60 holes, or about 45 to about 55 holes.

The vent 3400 may be located in or on the surface/barrier/shell of the plenum chamber 3200. Alternatively, or in addition thereto, the vent 3400 may be located in a decoupling structure e.g. a swivel 3510 (see FIG. 29) or a ball and socket 3520 (see FIG. 27*a*).

A vent arrangement, comprising one or a plurality of vents 3400 as described below may be located in the patient interface 3000, in the air circuit 4170 or as a separate component configured to be coupled to a patient interface 3000 or an air circuit 4170.

An exemplary gas washout vent 3400 according to an aspect of the current technology is shown in FIG. 7, showing a single vent 3400 which comprises a plurality of blades, or leaves 3404 and an outer housing 3408.

The vent 3400 may allow for a flow of breathable gas to traverse between either sides of the vent 3400 via a vent aperture 3422 as shown in FIG. 8. One aspect of the current technology is that the size of a vent aperture 3422 of a vent 3400 may be adjusted between a maximum size and a minimum size, allowing a plurality of configurations for the gas washout vent arrangement. Thus, aspects of the air flow therethrough may be adjusted and/or controlled by changing the size of the vent aperture 3422.

Aspects of the air flow through the vent 3400 may be modified by changing properties of the vent 3400, such as the size and/or orientation of the vent aperture 3422 or the components thereof. Examples of aspects of the air flow through the vent 3400 that may be modified by changing properties of the vent 3400 (such as the size of the vent aperture 3422) include the air impedance, or flow impedance, of the vent 3400 and/or characteristics of noise generated by the air flow as it flows through the vent 3400. For instance, the velocity of the flow of exhaust gas that is exhausted through the gas washout vent arrangement may be varied by varying the air impedance of the vent 3400. By varying the orientation of the components defining the vent aperture 3422, a direction of the air flow may be varied.

6.3.4.1 Vent Geometry

The size of the vent aperture 3422 may be described using a distance 'across faces', which is the distance across the aperture between the opposing faces of leaves 3404. An example of this measurement is shown in FIG. 24, wherein the distance designated DAF between a face of a leaf 3404(*a*) and a face of the opposing leaf 3404(*b*) would be a distance 'across faces. However, any number of other metrics may be used to describe the geometry. It is noted that although the faces of the leaves 3404 are shown as flat in FIG. 24, the face or surface of a leaf 3404 does not have to be flat and may have an alternative profile such as curved, jagged or tooth-shaped.

FIG. 9 shows an exploded view of the exemplary vent 3400 with a plurality of leaves 3404, a guiding member, or guide ring 3406, and an outer housing 3408. As illustrated, the vent 3400 may include six leaves 3404. However the vent may have any number of leaves 3404 as discussed in more detail below. The vent 3400 also may be connected to an actuating drive mechanism, which may include, for example, a magnet ring 3452 and a coil 3454. The actuating drive mechanism may take the form of any number of rotary or linear drive mechanisms, such as a linear actuator, a rotary actuator, a motor drive mechanism or any number of such means known in the art. The actuating drive mechanism may include the drive mechanism described in U.S. patent application Ser. No. 13/967609 filed on 15 Aug. 2013 or PCT/US2012/055148 filed on 13 Sep. 2012, the contents of which are incorporated herein in its entirety.

FIGS. 10-11 show further exploded views of the vent 3400 similar to that shown in FIG. 9, however showing different sizes of the vent aperture 3422. FIGS. 9-11 also show that each leaf 3404 can be coupled with the guide ring 3406, in that the guide ring 3406 is shown to have rotated as the vent aperture 3422 has changed in size. That is, partial rotation of the guide ring when coupled with the leaves will adjust the size of the opening of the vent aperture 3422. For example, in one direction, partial rotation of the guide ring will increase the opening in size and in the opposite direction, partial rotation of the guide ring will decrease the opening in size.

The guide ring 3406 includes a plurality of guide ring keys 3410 formed on the outer surface of the guide ring 3406 that are configured to each engage with a leaf guide slot 3412 (seen in FIG. 12*a*) formed on a first surface of each of the plurality of leaves 3404. A second surface of each of the plurality of leaves, such as an opposing surface to the first surface, is configured to couple to the outer housing 3408. Each of the plurality of leaves 3404 includes a leaf key 3414 located on a surface (such as the second surface) of each leaf 3404. Each leaf key 3414 may be inserted into an outer housing guide slot 3416, which may be a hexagonally edged slot or a slot with a number of edges corresponding to the number of leaves, formed in the outer housing 3408 as shown in FIG. 13. In some configurations as shown in FIG. 13 the leaf guide slots 3412 may be formed integrally with leaf keys 3414 such that the leaf guide slots 3412 are on a first surface and the leaf keys are on an opposing second surface. Alternatively (not shown) the leaf guide slots 3412 and the leaf keys 3414 may be on the same or adjacent surfaces.

FIGS. 12*a*-12*b* show a portion of the vent 3400 from a different angle to that of FIGS. 9-11, showing the plurality of leaves 3404 and the outer housing 3408 assembled together. These figures show the leaf guide slots 3412 that are formed on the first surface of each leaf 3404. Each leaf guide slot 3412 is configured to receive a guide ring key 3410 as described above.

FIG. 13 shows an exploded view of the vent 3400, only showing the plurality of leaves 3404 and the outer housing 3408 to display the outer housing guide slot 3416. It can be seen here that in this form, a movement of each individual leaf such as leaf 3404(3) follows a linear path (shown by the double ended arrow in FIG. 13) in the outer housing guide slot 3416 into which the leaf key 3414 (as shown FIG. 14*a*) is inserted along the edge of the slot. The outer housing guide slot 3416 is shown in FIG. 13 as a single continuous recess formed integrally with the outer housing 3408. However it may be formed as a plurality of discrete recesses, each configured to receive a leaf key 3414, and/or as a discrete component coupled to the outer housing 3408.

FIGS. 14a and 14b show the plurality of leaves 3404 (or a leave set) arranged to form an adjustable vent aperture 4322 according to one form of the current technology, showing two different sizes of the vent aperture 3422. FIG. 14b also illustrates a direction of exhaust flow at arrow EF through the leaves. FIG. 15 shows an example of one of the plurality of leaves according to an example of the present technology. In this example, the leaf key 3414 is integrally formed as a part of the leaf 3404, however it should be understood that it may alternatively be formed as a separate component that may be coupled between each of the plurality of leaves 3404 and the outer housing 3408.

As the plurality of leaves 3404 are moved from a configuration shown in FIG. 14a to a configuration shown in FIG. 14b, an outer leaf surface 3418 of one of the plurality of leaves 3404(1) slides relative to an inner leaf surface 3420 of an adjacent leaf 3404(2) of the plurality of leaves such as in a tongue and groove fashion. In this form, the coordinated movement of the plurality of leaves such as that between a leaf 3404(1) against an adjacent leaf 3404(2) result in the opening and closing of the vent aperture 3422 while maintaining a seal between the plurality of leaves 3404 other than in the area of the open vent aperture 3422.

Another aspect of the current technology is that it may allow for the vent aperture 3422 to be adjusted between a maximum size and a minimum size (e.g., limits). The maximum size and/or the minimum size may be predetermined in some cases, although the maximum and/or the minimum may be changed in other cases, for example to suit therapeutic need of each patient 100. The maximum size and/or the minimum size may be determined by the geometry of the vent 3400, or be otherwise determined or set such as by programming, or by adjustable switches for instance.

The predetermined minimum may be a zero area, or it may be a small area or any other value for the area, as will be described in more detail below. Another aspect of this technology is that the size of the vent aperture 3422 may be infinitely adjustable between the maximum and minimum sizes, subject to the resolution of the controller and/or the actuation/adjustment mechanism. In other cases, the vent 3400 may be arranged so that the size of the vent aperture 3422 may be one of a discrete number of sizes such as two, five, ten, fifteen or twenty for example.

A number of leaves 3404 may be used to construct the vent 3400. Accordingly, shape of the leaves 3404, shape of the outer housing guide slot 3416 and the shape of the aperture 3422 may be dependent on the number of leaves 3404 used in the vent 3400. For instance, the vent aperture 3422 shown in FIG. 14b is in a hexagonal shape as the vent 3400 has six leaves 3404 in this configuration. Preferably between three and eight leaves 3404 may be used in the vent 3400, more preferably between four and six leaves 3404 may be used, although the number of leaves 3404 may vary as the design parameters and requirements vary, such as the size of the required aperture, material employed or the cross-section profile of the leaf 3404.

In this arrangement of the current technology, each leaf guide slot 3412 is shaped as a rectangular slot with rounded internal corners. This facilitates slidable and rotatable movement of the corresponding guide ring key 3410 within each leaf guide slot 3412 when the plurality of leaves 3404 are moved to adjust the size of the vent aperture 3422. In this arrangement, the guide ring keys 3410 form a protrusion on the guide ring 3406 that is inserted into the leaf guide slots 3412 on each of the plurality of leaves 3404.

It will be understood that any number of other mechanisms known in the art may be used to perform in a similar manner to the couplings shown in the figures and/or described in this document. In an alternative arrangement, each of the plurality of leaves 3404 may include a protrusion or key (not shown) and the guide ring 3406 may include a slot or recess (not shown) that enables the slidable and rotatable movement of the protrusion or key located on each of the plurality of leaves 3404 as the plurality of leaves move. In a further alternative arrangement both of the guide ring 3406 and each of the plurality of leaves 3404 may include a slot or recess and a separate key component may be coupled therebetween. In a yet further alternative, both of the guide ring 3406 and each of the plurality of leaves 3404 may include protrusions or keys and a separate component comprising corresponding recesses or slots may be coupled therebetween.

In one form, each of the plurality of leaves 3404 comprises a leaf key 3414 on its second surface. The leaf key 3414 may have a shape with rounded internal corners to facilitate slidable movement of each of the plurality of leaves 3404 relative to the outer housing 3408, although any number of other arrangements may be used to perform in a similar manner. As described above, the outer housing 3408 includes an outer housing guide slot 3416 configured to receive the leaf keys 3414 from one of the plurality of leaves 3404 therein. The outer housing guide slot 3416 is larger than the size of the leaf keys 3414 to facilitate movement of the connecting plate protrusions along the outer housing guide slot 3416 when the plurality of leaves 3404 are moved to adjust the size of the vent aperture 3422.

In an alternative arrangement, the outer housing 3408 may comprise keys and each of the plurality of leaves may include a slot or recess that enables the slidable movement of the keys located on the outer housing 3408 within the slots or recesses on the plurality of leaves 3404 as the plurality of leaves 3404 move. In a further alternative arrangement both of the outer housing 3408 and each of the plurality of leaves 3404 may include a slot or recess and a separate connecting plate component may be coupled therebetween. In a yet another alternative arrangement both of the outer housing 3408 and each of the plurality of leaves 3404 may include keys and a separate connecting component comprising recesses or slots may be coupled therebetween.

6.3.4.2 Vent Controller

In another aspect of the present technology, a controller, such as one with a processor(s) and which may optionally serve as a processor or controller of a RPT device, may be configured to control the one or more vents 3400 such as a vent arrangement described herein. In one form, the controller may be configured, e.g., programmed, to perform one or more of the methods or algorithms described throughout this specification, such as to control aspects of the one or more vents 3400. For example, it may control the size and/or orientation of its apertures 3422. Such control may be, for example, based on one or more inputs as described in further detail herein. Such a device controller or processor may, for example, include integrated chips, such as application specific integrated chip(s), a memory and/or other control instruction, data or information storage medium with the methodologies. Thus, programmed instructions encompassing the methodologies may be coded on integrated chips or in the memory of the device. Such instructions may be loaded as software or firmware using an appropriate data storage medium. The controller may then be in electrical communication with a controllable actuator or actuation mechanism as described herein for automated manipulation of the components of vent (e.g., guide ring and/or leaves).

In one form, a size of the vent aperture 3422 may be adjusted by rotationally constraining the outer housing 3408 and affixing the guide ring 3406 to an actuator, which may be controlled by the controller. The actuator may then rotate the guide ring 3406 to adjust the size of the vent aperture 3422. The controller may be configured to receive an indicative signal such as from the actuator and/or a discrete sensor regarding a property of the vent 3400, such as a signal indicating an orientation and/or the size of the aperture 3422. The actuator may be further configured to determine when the size of the vent aperture 3422 of the vent 3400 has reached the predetermined maximum or the predetermined minimum throughout its range of possible sizes. In one form, the actuator may include limit switches configured to detect when the vent aperture 3422 is at the minimum and/or the maximum size.

One aspect of the method of operation of the vent aperture controller may be to control performing one or more calibration cycles with the vent 3400. According to one form of the calibration cycle, shown in FIG. 23a, the first calibration cycle 34710 may be performed to determine one of the vent's limits, such as a 'completely open' position, or a position of maximum size of the vent aperture 3422. In such a first calibration cycle 34710, the actuator 3480 may be instructed to progressively open the vent 3400 in step 34712, while measuring the current required in the actuator in step 34714 and comparing the measured current ($I_{meas}$) in relation to a limit current ($I_{limit}$) threshold in step 34716. When the current limit is exceeded, the actuator may be stopped (step 34717) and the position may be recorded in step 34719. Thus, the first calibration cycle 34710 would continue until the size of the vent aperture 3422 reaches its maximum, upon which point the controller (using the limit switch for instance) may detect an indicative position signal such as the voltage supplied exceeding a threshold voltage, or the current supplied exceeding a threshold current, or the power supplied exceeding a threshold power, or a proximity sensor indicating that the vent is at its 'completely open' position.

According to another form of the calibration cycle, shown in FIG. 23b, the second calibration cycle 34720 may be performed to determine the other limit of the vent such as a 'completely closed' position, or a position of minimum size of the vent aperture 3422. In the second calibration cycle 34720, the actuator 3480 may be instructed to progressively close the vent 3400 in step 34722 until the aperture 3422 reaches its minimum, upon which point the limit switch may detect an indicative position signal such as those described above (current, voltage and/or power). The first calibration cycle 34710 and the second calibration cycle 34720 may thus provide a controller with accurate limits of travel for the leaves of the vent and thus the aperture 3422. Although these calibration cycles have been described in a particular order, they may be reversed such that the first cycle may determine a fully closed position and the second cycle may determine a fully open position. Furthermore, a skilled addressee would understand that other calibration steps to determine different positions of the leaves of the vent may also be undertaken.

Another aspect of the current technology is that the minimum size of the vent aperture 3422 may be so small so as to have zero area. Any number of sizes may be chosen for the minimum size of the vent aperture 3422 such as a size between, for example, 0.01 mm to 10 mm distance across faces, such as 0.1 mm, 0.5 mm or 2 mm, 4 mm, 6 mm or 8 mm distance across faces.

According to another aspect of the present technology, the controller may be in communication with one or more sensors and/or the vent arrangement to send and/or receive suitable control and/or sensing signals. In some cases, the controller may be a central controller 4230 that forms a part of the RPT device and performs other functions. However, the controller may optionally be a standalone vent controller 3438 configured only to be in communication with the sensors and/or the vent arrangement. In some such cases, for example, the controller may be placed on or in a patient interface or the air circuit. Such a standalone vent controller 3438 may optionally be in communication with a central controller 4230 as shown in FIG. 4c such as to be controlled by commands from the central controller.

6.3.4.3 Cross-Section Profile

As described above, some of the problems related to prior vent technologies concern noise. Some may be noisy, which may disturb the patient 1000, and/or that they may be disruptive to the sleep of a bed-partner 1100 as a result of the passage of air through the vent.

Thus, in some forms of the present technology, the vent may be configured so that as the size of the aperture 3422 changes, the cross-section profile of each outer leaf surface 3418 that is exposed to the flow of breathable gas traversing through the vent remains constant. In some configurations, the cross-section profile may remain constant irrespective of the length of the outer leaf surface 3418 that is exposed to the flow of breathable gas. Therefore, one advantage of the present technology may be that a cross-section profile may be chosen to reduce the noise generated by the gas washout vent arrangement, which may reduce disruption caused to the user and/or the bed partner of the user. The cross-section profile design can be important for reducing noise.

Assuming a unidirectional air flow, one suitable example design of the cross-section profile 3424 of the outer leaf surface 3418 of each of the plurality of leaves 3404 may be as shown in FIG. 16. The cross-section profile of each outer leaf surface 3418 that is exposed to the flow of breathable gas remains constant as the size of the vent aperture 3422 changes as described above. Therefore, the cross-section profile 3424 may be shaped at the leading edge 3426 and the trailing edge 3428 to reduce noise generated by the flow of breathable gas as it passes through the aperture 3422. In such a case, the vent may be oriented for use with the unidirectional airflow passing over the outer leaf surface 3418 starting at the leading edge 3426 then proceeding across the surface and then proceeding past the trailing edge 3428.

One suitable cross-section profile may be a 'reverse-trumpet' profile, similar to one disclosed in the US patent application US 2010/0051034, the entire contents of which is incorporated herein by reference.

Such a profile may include a contracting, curved leading edge 3426 that blends into the entry side surface 3430 of each of the plurality of leaves 3404. The profile may further include a sharply terminating trailing edge 3428 at the exhaust side surface 3432 as shown in FIG. 16. The leading edge 3426 may approximate a contracting curved surface and connect to the trailing edge 3428, which may be curved and tangential to a centre axis of the aperture 3422 or converge at a small angle, such as between approximately 0 and approximately 15 degrees. The trailing edge may terminate with an angle of between approximately 60 degrees and approximately 100 degrees, such as 70 degrees, 80 degrees, or 90 degrees between the exit-side surface 3432 of the leaf 3404 and the trailing edge 3428.

The radius of the leading edge R2 may be between approximately 0.5 mm and approximately 1.5 mm, such as 0.75 mm, 1 mm or 1.25 mm, and the radius of the trailing edge R1 may be between approximately 1 mm and approximately 3 mm, such as 1.5 mm, 2 mm or 2.5 mm. The thickness T1 of each leaf 3404 may be between approximately 1 mm and approximately 4 mm, such as 2 mm, 2.5 mm or 3 mm. The convergence, in section depth C1 of each of the plurality of leaves 3404 may be between approximately 0.5 mm and approximately 2.5 mm, such as 1 mm, 1.5 mm or 2 mm. In other arrangements of the present technology, where a vent arrangement is configured to allow air flow in either direction of the vent arrangement, a symmetric cross section profile may be preferred.

In one instance of the present technology, the vent 3400 may consist of six leaves 3404, wherein the thickness T1 of each leaf 3404 may be about 1-4 mm, such as 2 mm, 2.5 mm or 3 mm, and the maximum distance across each opposing leaves (across faces) may be about 5-15 mm, such as 6 mm, 8 mm, 10 mm, 12 mm or 14 mm. In this arrangement, the vent 3400 with the aperture 3422 at the most open position would be approximately between 21 mm$^2$ and 195 mm$^2$ such as 30 mm$^2$, 55 mm$^2$, 80 mm$^2$, 125 mm$^2$ or 170 mm$^2$ depending on the distance across faces and at 7 mm distance across faces (AF) the area of the aperture 3422 may be approximately 42 mm$^2$.

Another aspect of the present technology is that characteristics of noise generated by the flow of breathable gas through the vent 3400 may change as the size of the vent aperture 3422 changes. One example of such a noise characteristic is the level of noise generated, although other characteristics such as the frequency content of the noise may also change. An example showing changes to the measured sound power level as a function of the aperture 3422 size (distance across faces) and/or the pressure is shown in FIG. 25 for one form of the present technology vent 3400. For example, at approximately 10 cm H$_2$O of pressure, the measured sound power level of an example of the vent 3400 was approximately 30 dBA when the vent 3400 was configured with a distance across faces of approximately 4 mm. When the vent 3400 was in another configuration with a distance across faces of approximately 7 mm, the measured sound power level was approximately 32 dBA. To take advantage of the changing noise characteristic of the vent 3400, a plurality of vents 3400 and/or sensors may be implemented in some embodiments of the technology as will be shown in further detail below.

The dimensions of the vent 3400 may be varied under different design circumstances, such as when varying the number of vents 3400 to be placed on/in a patient interface 3000, or when varying therapy requirements. As a result, the dimensions as described above should be understood to be only exemplary and a person skilled in the art would be capable of changing any number of the above dimensions of the vent 3400 to suit their requirements.

6.3.4.4 Vent Arrangements (e.g., Sensor Enabled)

In another aspect of the current technology, a vent arrangement comprising vents 3400 such as those described above, and/or other adjustable (active) and non-adjustable vents, may be used to ameliorate problems known in the art described above. Such problems to be ameliorated may include potential sources of discomfort and/or disruption caused to the patient 1000 and/or the bed-partner 1100. The potential sources of discomfort and/or disruption may include noise generated by the flow of breathable gas, whether as it passes through a vent arrangement or after it passes through a vent arrangement, and jetting of flow of air onto the patient 1000 and/or onto the bed-partner 1100. In one form, one or more signals indicative of potential disruption may be communicated from one or more sensors to a controller, such as any of the controllers described in this specification, which may be used to adjust the vent arrangement accordingly.

In one form, a gas washout vent arrangement may include multiple instances of the vents 3400 (e.g., a set of vents 3400) described above to be placed in fluid communication with a patient interface 3000 such as one or more of: in the plenum chamber 3200, or in a decoupling structure 3500, or in the air circuit 4170, or in between the patient interface 3000 and the air circuit 4170. Properties of the set of the vents 3400 may then be controlled together or separately (e.g., one, more or all of the set) to control various properties of the flow of breathable gas communicating through the patient interface 3000, such as noise generated by the flow or a direction of the flow. An example of adjusting the apertures 3422 may be by selectively moving the movable portions of the vent arrangement, which may then change flow impedances of the multiple vents 3400 (e.g., one or more of the set).

In some instances, such a vent arrangement may be used to adjust the noise generated from the flow of breathable gas through each vent 3400 or vary the amount of flow through the vent 3400 during different phases of the respiratory cycle. For example, the vents may be configured to open only during the expiration phase of the respiratory cycle.

In one form of the present technology, two vents 3400 may be placed on either side of the patient interface 3000 as shown in FIG. 22. In this example the two vents 3400 are positioned approximately symmetrical about the sagittal plane once the patient 1000 puts on the patient interface 3000. However, the vents may be located in other positions on the patient interface 3000 as discussed further below.

One control method of achieving noise reduction may be to vary the size and/or orientation of the aperture 3422 of a vent arrangement (e.g. each vent 3400) according to one or more predetermined control parameter(s). One example of such a control parameter may be measured noise levels from microphones 3440 placed near each vent 3400. In another example of a suitable control parameter may be an output from an accelerometer 3442, which may be processed to indicate an orientation of the patient 1000 or the patient interface. Other suitable control parameters may include, pressure, flow, temperature, respiratory phase, such as whether the patient is in inspiration or in expiration, or therapy-related parameters, such as the patient's SpO2 level or whether the patient suffers from CSR.

An exemplary set of locations of microphones 3440 or proximity sensors 3444 placed near each vent 3400 or an accelerometer(s) 3442 is shown in FIG. 22, however it is to be understood that the numbers and locations of the vents 3400, the microphones 3440, or accelerometer(s) 3442 may be varied. Any number of other sensors known in the art, such as pressure, temperature or flow sensors may be used to provide one or more control parameters. For example, one or more sensors to detect orientation of the patient interface may be implemented and the opening or closing of one or more of the vents may be selected/controlled depending on the detected orientation of the patient interface. In some such cases, the controller may open or increase the aperture of a vent(s) on a upwardly oriented side of the mask and close or decrease the aperture of a vent on a downwardly oriented side of the mask or vice versa. Thus, the vents on opposing sides of the patient interface/mask may be controlled differently and/or may implement dynamic selection of the direction of venting of the mask so as to re-direct exhaust flow in different directions relative to the patient interface.

FIG. 26a-26b shows another form of the current technology, including a vent 3400 comprising a plurality of holes and a movable portion 3456 which is movable relative to the vent 3400 allowing a plurality of configurations for the gas washout vent arrangement. In this form, the movable portion 3456 may be moved to adjust properties of the vent 3400. For instance, the plurality of holes in the vent 3400 may be configured so that the flow impedance of the vent 3400 may vary depending on the position of the movable portion 3456 (e.g. it may slide to cover/block more or fewer of the plurality of holes). Such movement or sliding may be implemented through manual adjustment of movable portion or in response to movement and/or orientation of the patient interface itself.

For example, the vent 3400 may be configured so that the direction of the flow of air therethrough may differ depending on the position of the movable portion 3456 as shown in FIG. 26a-26b. For example, where the removable portion 3456 of a vent 3400 is in a configuration as shown in FIG. 26a, the flow of exhaust gas may be generally directed towards the left side of the mask, whereas in FIG. 26b the flow of exhaust gas may be generally directed towards the right side of the mask. In this regard, the dotted lines in FIG. 26a-28b and FIG. 30a-30b illustrate a change in direction (re-direction) of the flow of exhaust gas as it is exhausted from the patient interface responsive to the re-positioning of the movable portion.

Alternatively, or additionally, some of the holes of the vent may be configured for inward flow only and some of the hole of the vent may be configured for outward flow only such as with a one way valves. Thus, when the slide is moved vent may selectively permit inward flow and/or outward flow.

Such a vent 3400 may then be configured be adjusted based on one or more control parameters, such as outputs from one or more sensors such as a microphone 3440 or an accelerometer 3442 and/or in some cases the vent(s) may be adjusted by the gravitational orientation of the mask.

For instance, the movable portion 3456 in such a vent 3400 shown in FIG. 26a and FIG. 26b may be configured to slide according to an orientation of the patient. This may be implemented by the use of an accelerometer as described above and a suitable actuator, or by configuring the movable portion 3456 to slide due to gravity (e.g., weighted movement of the sliding moveable portion) following orientation of the vent 3400. FIG. 29 shows an instance where the patient 1000 is lying in a bed with her head tilted towards her left. Accordingly, the movable portion 3456 becomes oriented towards the left side of the patient 1000, changing the direction of the flow of exhaust air away to be away from the bed. In some cases, the movable portion may include additional weights to overcome static friction and/or airflow in order for the movable portion 3456 to slide relative to the vent 3400. FIG. 27a and FIG. 27b show another type of a patient interface 3000 (nasal mask) which incorporates a vent 3400 including a movable portion 3456.

In another form, the vent 3400 may be configured as shown in FIG. 28a and FIG. 28b. The vent 3400 in FIG. 28a includes one or more of a movable portion 3456 in the form of a prism or ball, and configured to move along or within one or more of a guiding portion 3458 such as an open ended channel CC. Optionally, each of the open ends (OE1, OE2) may comprise a plurality of holes to vent air from the plenum chamber and a portion of the channel CC (e.g., an inside portion) may be in air communication with the air of the plenum chamber. Thus, the guiding portion 3458 may comprise a plurality of apertures, such as at a first end of the guiding portion and a second end of guiding portion, which (or portions thereof) may be opened and/or closed according to a movement of the movable portion 3456. For example, by re-positioning the orientation of the patient interface such that the guiding portion or channel will have a lower end and a higher end. As a result, gravity may re-position the weighted prism or ball to the lower end (e.g., by sliding or rolling in and along the channel) of the guiding portion or channel so that the prism or ball will move to seal or partially seal the lower end of the guide portion or channel and thereby open or increase the opening of the higher end for exhaust venting. In this way and similar to other movable portion embodiments described herein, the flow of the exhaust venting may be periodically re-directed from one side of the patient interface to the other, enforcing an upward (e.g., away from mattress) venting direction even as the mask is re-positioned from one side to another as the patient, wearing the patient interface, rolls in bed. In some cases, repositioning may cause the movable portion to be more centrally located between the ends of the guiding portion (e.g., when a patient with the patient interface is lying on his/her back). As such, venting flow at both open ends depending on the vent characteristics may be reduced since the moveable portion is blocking neither end. This dual end open situation may reduce vent flow at both ends including the end in a direction of a bed partner when compared to a situation when only one end is blocked and one end is open. Of course, such venting schemes may also be enforced with one or more orientation sensors and electro-mechanical control of different vents (such as any of the vents disclosed in this specification) on opposing sides of the patient interface or one or more of such vents configured to change exhaust flow direction.

In a yet another form, the vent 3400 may include a movable portion 3456, as shown in FIG. 30a and FIG. 30b, where the movable portion 3456 includes one or more holes for washout of exhaust gas. In the arrangement shown in FIG. 30a and FIG. 30b, the movable portion 3456 includes an aperture 3457 to allow fluid communication between the inside of the plenum chamber 3200 and the ambient environment. The moveable portion forms a swivel that can pivot, such as by mechanical actuator (such as a stepper motor with a gear coupled with a side of the swivel to rotate the swivel) and/or gravitation rotation (e.g., weighted on one side of the swivel or counter balanced). In this regard, a flow channel FC of the swivel with an inside opening CIO to the plenum chamber can rotate with the swivel to change the direction from which flow exits the aperture of the swivel. Thus, when the patient interface is re-oriented such as from side to side, flow can be re-directed, such as to enforce an upward flow (e.g., away from mattress) or away from the patient's bed partner. Accordingly, the movable portion 3456 may move in response to one or more control parameters, such as outputs from one or more sensors such as a microphone 3440 or an accelerometer 3442 or due to patient orientation resulting in adjustment or movement of the aperture 3457.

Of course, any vent configured with one or more adjustable properties of the vent, such as a direction of air flow therethrough or the pneumatic impedance, may be used in conjunction with one or more sensors and/or the control methodologies as described above. For example, any number of vents disclosed in PCT patent application number PCT/US2012/055148 may be implemented with the above aspect(s) of the present technology.

According to another aspect of the present technology, the one or more signals indicative of potential disruption (e.g., vent related noise) may be correlated with an indicator of disruption to the patient 1000 and/or the bed-partner 1100. In one form, an indicator of arousal such as those known in the art (e.g., one detected by processor analysis of a flow signal and/or a signal from a movement sensor) may be correlated with the indicator of disruption. In such a case, the controller may be configured to control adjustments to the vent arrangement based on the arousal indicator and the disruption indicator. For example, the processor may control changes to the vent when arousal is indicated and the signal(s) indicative of potential disruption such as noise is above a threshold. One example of prior art documenting detecting indicators of arousal in the prior art may be in the PCT patent application WO 2011/006199, the contents of which are incorporated herein by cross-reference. Detection of arousal then may be combined with any of the above indicators of potential disruption in order to better determine whether the potentially disruptive indicators would warrant an adjustment to the vent arrangement.

6.3.4.4.1 Example Control Functions

A number of example control functions are described below. Such methodologies may be implemented by any of the controllers described throughout this specification. Although the control functions may be drawn and/or described based on a specific number of vents 3400 and/or configurations of vents 3400, it should be understood that they may be adapted to suit any number of vents 3400 and/or configurations of vents 3400 while still taking advantage of the present technology.

6.3.4.4.1.1 Vent Aperture Sizing Control Function A 34610

FIG. 17 shows a flow chart of one form of a vent aperture sizing control function 34610 for controlling a size of the aperture 3422. The vent aperture sizing control function A 34610 may control the size of the aperture 3422 of each vent 3400 as a function of one or more control parameters, for example such as those described above. In step 34612, the vent aperture sizing control function A 34610 may determine value(s) of the control parameter. The value(s) of the control parameter may comprise, for example, noise levels as measured by the microphones 3440 placed near each vent 3400 and/or a signal indicating the orientation of the patient 1000, or other inputs as described above. The vent aperture sizing control function A 34610 may determine desired opening sizes in step 34614 for apertures 3422, for instance based on the value(s) of the control parameter(s). Step 34614 may be carried out using a look-up table or a predetermined vent sizing function configured to determine desired changes to vent sizing based on the inputs of the value(s) of the control parameter(s). The vent aperture sizing protocol may then communicate in step 34616 the desired aperture opening sizes (or other suitable control signal) to the controller's actuator to adjust the sizes of each vent apertures 3422 accordingly.

6.3.4.4.1.2 Vent Aperture Sizing Control Function B 34620

Another form of a vent aperture sizing function is shown as a flowchart in FIG. 18. The vent aperture sizing control function B 34620 is described based on two vents 3400 in a vent arrangement (e.g. as shown in FIG. 22). In this form, the vent aperture sizing control function B 34620 may open both vents 3400 in step 34622 to ensure equal operating conditions for the vents 3400. As a next step 34624, the control function B 34620 may determine noise levels (N1 and N2), for example by measurement at two microphones 3440 that are placed near each vent 3400 as shown in step 34623. The vent sizing function may then compare the noise levels N1 and N2 in step 34626, and in step 34628 act to close or partially close the vent 3400 that is creating more noise.

6.3.4.4.1.3 Vent Aperture Sizing Control Function C 34630

Another form of a vent aperture sizing function is shown as a flowchart in FIG. 19, where the vent arrangement comprises two vents 3400 (e.g. as shown in FIG. 22). In step 34632, the vent aperture sizing control function C 34630 may determine noise levels N1 and N2, respectively at each vent 3400. The control function C 34630 may determine two noise levels (N1 and N2) in step 34631, for example by receiving data or signals representing them from two microphones 3441) that are placed near each vent 3400. The control function C 34630 may also receive data or signals representing areas of apertures 3422 (S1 and S2) from each vent 3400 for example from step 34638. The vent sizing function would compare the noise levels N1 and N2 in step 34634, and step 34638 may adjust the sizes of the aperture 3422 based on a difference in noise levels N1 and N2. A threshold step 34636 may be included so that the step 34638 may only be activated if the difference in noise levels N1 and N2 exceed a difference threshold $\Delta N_{threshold}$.

In one form of the step 34638, the control function C 34630 may act to reduce the size of the aperture 3422 of the corresponding vent 3400 where the noise level was found to be higher, and/or increase the size of the aperture 3422 of the corresponding vent 3400 where the noise level was found to be lower. Furthermore, the size of the aperture 3422 of each vent 3400 may be adjusted by a predetermined increment until the noise levels N1 and N2 are substantially equal to each other, or until the difference in noise levels is under a predetermined threshold.

Yet further, in the vent sizing functions described above, the function may also compare the noise levels N1 and N2 against a threshold value $N_{threshold}$ and only adjust the size(s) of the vent aperture(s) 3422 if one or both values are above and/or below $N_{threshold}$.

6.3.4.4.1.4 Vent Aperture Sizing Control Function D 34640

Another form of a vent sizing function is shown as a flowchart in FIG. 20. In this example, the vent aperture sizing control function D 34640 may determine an orientation of a patient 1000 in step 34642. For instance, the vent control function D may receive a signal in step 34641 indicating at least one of the orientation of the patient 1000 or the orientation of the patient interface 3000 from an accelerometer 3442. The vent aperture sizing control function D 34640 may then adjust the sizes of vent apertures 3422 in step 34644 based on the orientation determined in step 34642.

For instance, in operation, the step 34644 may send a signal to the vents 3400 to reduce the size of the aperture 3422 of the corresponding vent 3400 which is closer to the ground (e.g., vent oriented downward), and increase the size of the aperture 3422 of the corresponding vent 3400 which is further from the ground (e.g., vent oriented upward). Adjustment of vent aperture size according to patient orientation as in sizing control function D 34640 may reduce noise generated by the patient interface 3000 from impingement of the flow of breathable gas. Such noise may be generated from impingement upon an obstruction such a pillow, or bedding is known to generate additional noise in comparison to the unobstructed flow of breathable gas exiting the vent 3400 exits into the atmosphere.

Furthermore, by adjustment of vent aperture size according to patient orientation as in sizing control function D 34640, it may also be possible to reduce the amount of exiting flow of breathable gas from a vent 3400 that is directed at a bed partner 1100, which may reduce annoyances and/or additional noise experienced by the bed partner. For example, the controller may include an input setting to indicate which side of the bed on which a patient sleeps relative to bed partner 1100. In the event that the controller detects an orientation of the patient interface, such as with the orientation sensor(s)/accelerometer(s), that indicates that the patient 1000 is sleeping on his/her back, the controller may then, based on the setting, reduce the flow of venting on the side of the bed partner. For example, the controller may then select to open or open more a vent of the patient interface opposite the bed partner and/or close or open less a vent of the patient interface adjacent to the bed partner.

In another form of the present technology (not shown), the vent aperture sizing control function may receive a signal from a proximity sensor 3444 indicating the proximity of the patient 1000 to its bed partner 1100 or another obstruction to each vent 3400 in the direction of its aperture 3422. The vent sizing function may then act to adjust sizes of the vent apertures 3422 accordingly, such as reduce the size of the aperture 3422 of the corresponding vent 3400 which is closer to the bed partner 1100 or obstruction, and increase the size of the aperture 3422 of the corresponding vent 3400 which is further from the bed partner 1100 or obstruction. It is to be understood that the vent sizing function may also receive and react to a signal from other types of sensors, such as from a modulated pulse Doppler based sensor such as one disclosed in U.S. Pat. No. 6,426,716 or a sensor described in US patent application number 2009/0203972, the entire contents of which are included herein by reference. Such a sensor may serve as a proximity sensor and/or orientation sensor in some versions of the present technology.

In a yet another example of the current technology, the vent aperture sizing control function may receive and react to a signal indicating whether the patient 1000 is in an inspiration phase or in expiration phase of the breathing cycle. According to this signal the vent sizing function may, for example, close the vent 3400 during the inspiration phase of the patient's breath, and open the vent 3400 during the expiration phase of the patient's breath.

Although a number of above paragraphs discuss means of determining sizes of apertures 3422 of vents 3400 using a vent aperture sizing control 'function', it should be understood that use of the term 'function' does not preclude use of a multi-dimensional look-up table by themselves or in conjunction with a mathematical function.

6.3.4.4.1.5 Vent Aperture Sizing Control Function E 34650

Another instance of the current technology that utilises a look-up table is shown in FIG. 21. This vent aperture sizing control function E 34650 may determine noise levels N1 and N2 near each vent 3400 in step 34652, possibly using measurements from sensors such as microphones in step 34651. A differential noise value Nd, may be calculated in step 34653 as a difference between the two noise levels N1 and N2, which may be compared against a threshold $N_{threshold}$ in step 34654. An amount by which to adjust the size of the aperture 3422 ($\Delta$Area) may be determined (for example from a look-up table) as shown in step 34655, and the vent aperture sizes may be adjusted based on this value in step 34656. The adjusted, resulting sizes of vent apertures 3422 may also be passed on to step 34652 as an input from step 34656.

It is to be understood that the control protocols and means described above are not to be limited only to the instance of the current vent 3400 and vent arrangement technology. A comparable performance to adjusting sizes of vent apertures 3422 of multiple vents 3400 according to sensor inputs may be also performed by a single vent assembly that allows the flow of breathable air to be re-directed. For instance, a single vent assembly that has an actuator for movement of its vent aperture along the sagittal plane may allow the vent to direct its outflow to the left or the right side of the patient 1000 according to a sensor input as described above and/or according to any of the adjustment control methodologies described herein.

6.3.5 Decoupling Structure(s)

In one form the patient interface 3000 includes at least one decoupling structure, for example a swivel 3510 (see FIG. 29) or a ball and socket 3520 (see FIG. 27a).

6.3.6 Connection Port 3600

Connection port 3600 allows for connection to the air circuit 4170.

6.3.7 Forehead Support 3700

In one form, the patient interface 3000 includes a forehead support 3700.

6.3.8 Anti-Asphyxia Valve

In one form, the patient interface 3000 includes an anti-asphyxia valve.

6.3.9 Ports

In one form of the present technology, a patient interface 3000 includes one or more ports that allow access to the volume within the plenum chamber 3200. In one form this allows a clinician to supply supplemental oxygen. In one form this allows for the direct measurement of a property of gases within the plenum chamber 3200, such as the pressure.

6.4 RPT Device 4000

An example RPT device 4000 that may be suitable for implementing aspects of the present technology may include mechanical and pneumatic components 4100, electrical components 4200 and may be programmed to execute one or more of the control methodologies or algorithms described throughout this specification. The RPT device may have an external housing 4010, preferably formed in two parts, an upper portion 4012 of the external housing 4010, and a lower portion 4014 of the external housing 4010. In alternative forms, the external housing 4010 may include one or more panel(s) 4015. Preferably the RPT device 4000 comprises a chassis 4016 that supports one or more internal components of the RPT device 4000. In one form a pneumatic block 4020 is supported by, or formed as part of the chassis 4016. The RPT device 4000 may include a handle 4018.

The pneumatic path of the RPT device 4000 preferably comprises an inlet air filter 4112, an inlet muffler 4122, a controllable pressure device 4140 capable of supplying air at positive pressure (preferably a blower 4142), and an outlet muffler 4124. One or more pressure sensors 4272 and flow sensors 4274 are included in the pneumatic path.

The preferred pneumatic block 4020 comprises a portion of the pneumatic path that is located within the external housing 4010.

The RPT device 4000 preferably has an electrical power supply 4210, one or more input devices 4220, a central controller 4230, a therapy device controller 4240 and/or any of the controllers previously described, a pressure device 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

The central controller 4230 of the RPT device 4000, which may include one or more processors, can be programmed to execute one or more algorithm modules, preferably including a pre-processing module, a therapy engine module, a pressure control module, and further preferably a fault condition module. It may further include a vent control module that may be configured with one or more of the vent control methodologies described throughout this specification.

6.4.1 RPT Device Mechanical & Pneumatic Components 4100

6.4.1.1 Air Filter(s) 4110

A RPT device in accordance with one form of the present technology may include an air filter 4110, or a plurality of air filters 4110.

In one form, an inlet air filter 4112 is located at the beginning of the pneumatic path upstream of a blower 4142. See FIG. 4*b*.

In one form, an outlet air filter 4114, for example an antibacterial filter, is located between an outlet of the pneumatic block 4020 and a patient interface 3000. See FIG. 4*b*.

6.4.1.2 Muffler(s) 4120

In one form of the present technology, an inlet muffler 4122 is located in the pneumatic path upstream of a blower 4142. See FIG. 4*b*.

In one form of the present technology, an outlet muffler 4124 is located in the pneumatic path between the blower 4142 and a patient interface 3000. See FIG. 4*b*.

6.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 liters/minute, at a positive pressure in a range from about 4 cm $H_2O$ to about 20 cm $H_2O$, or in other forms up to about 30 cm$H_2O$.

The pressure device 4140 is under the control of the therapy device controller 4240.

6.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path, In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

6.4.1.5 Anti-Spill Back Valve 4160

In one form of the present technology, an anti-spill back valve is located between the humidifier 5000 and the pneumatic block 4020. The anti-spill hack valve is constructed and arranged to reduce the risk that water will flow upstream from the humidifier 5000, for example to the motor 4144.

6.4.1.6 Air Circuit 4170

An air circuit 4170 in accordance with an aspect of the present technology is constructed and arranged to allow a flow of air or breathable gasses between the pneumatic block 4020 and the patient interface 3000.

6.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

6.4.2 RPT Device Electrical Components 4200

6.4.2.1 Power Supply 4210

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000. The power supply may also optionally provide power to any actuator, controller and/or sensors for a vent arrangement as described throughout this specification

6.4.2.2 Input Devices 4220

In one form of the present technology, a RPT device 4000 includes one or more input devices 4220 in the form of buttons, switches or dials to allow a person to interact with the device. These may be implemented for entering settings for operation of the components of the RPT device such as the vent arrangement. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

6.4.2.3 Central Controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

In another form of the present technology, the central controller 4230 is a processor suitable to control a RPT device 4000 such as an x86 INTEL processor.

A processor of a central controller 4230 suitable to control a RPT device 4000 in accordance with another form of the present technology includes a processor based on ARM Cortex-M processor from ARM Holdings. For example, an STM32 series microcontroller from ST MICROELECTRONICS may be used.

Another processor suitable to control a RPT device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor for the RPT device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

In some forms of the present technology, the processor of the central controller 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a RPT device 4000. However, in some forms of the present technology the processor(s) may be implemented discretely from the flow generation components of the RPT device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein. Similarly, such a processor may perform any of the methodologies described herein for purposes controlling operation of any vent arrangement described in this specification.

6.4.2.4 Clock 4232

Preferably RPT device 4000 includes a clock 4232 that is connected to processor.

6.4.2.5 Therapy Device Controller 4240

In one form of the present technology, therapy device controller 4240 is a pressure control module 4330 that forms part of the algorithms 4300 executed by the processor of the central controller 4230.

In one form of the present technology, therapy device controller 4240 is a dedicated motor control integrated circuit. For example, in one form a MC33035 brushless DC motor controller, manufactured by ONSEMI is used.

6.4.2.6 Protection Circuits 4250

Preferably a RPT device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

6.4.2.7 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, RPT device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

6.4.2.8 Transducers 4270

Transducers may be internal of the device, or external of the RPT device. External transducers may be located for example on or form part of the air delivery circuit, e.g. the patient interface. External transducers may be in the form of non-contact sensors such as a Doppler radar movement sensor that transmit or transfer data to the RPT device.

6.4.2.8.1 Flow

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the processor.

6.4.2.8.2 Pressure

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the central controller processor. In one form, the signal from the pressure transducer 4272 is filtered prior to being received by the central controller 4230.

6.4.2.8.3 Motor Speed

In one form of the present technology a motor speed signal 4276 is generated. A motor speed signal 4276 is preferably provided by therapy device controller 4240. Motor speed may, for example, be generated by a speed sensor, such as a Hall effect sensor.

6.4.2.9 Data Communication Systems 4280

In one preferred form of the present technology, a data communication interface 4280 is provided, and is connected to central controller processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor of central controller 4230. In another form, data communication interface 4280 is an integrated circuit that is separate from the central controller processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

6.4.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

6.4.2.10.1 Display Driver 4292

A display driver 4292 receives as an input the characters, symbols, or images intended for display on the display 4294, and converts them to commands that cause the display 4294 to display those characters, symbols, or images.

6.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

6.5 Glossary

In certain forms of the present technology, one or more of the following definitions may apply. In other forms of the present technology, alternative definitions may apply.

6.5.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

6.5.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

6.5.3 Aspects of a Patient Interlace

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load hearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a patient interface plenum chamber will be taken to mean a portion of a patient interface having walls enclosing a volume of space, such as for a full-face mask (e.g., nose and mouth mask), a nasal mask or a nasal pillow, the volume having air therein pressurised above atmospheric pressure in use by the patient. A shell may form part of the walls of a patient interface plenum chamber. In one form, a region of the patient's face abuts one of the walls of the plenum chamber, such as via a cushion or seal.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

6.6 Other Remarks

A portion of the disclosure of this patent document contains material which is subject to copyright protection.

The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

REFERENCE SIGNS LIST 1000 patient
1100 bed-partner
3000 patient interface
3100 seal-forming structure
3200 plenum chamber
3210 perimeter
3300 structure
3400 vent
3404 leaf
3406 guide ring
3408 outer housing
3410 guide ring key
3412 guide slot
3414 leaf key
3416 outer housing guide slot
3418 outer leaf surface
3420 inner leaf surface
3422 aperture
3424 section profile
3426 leading edge
3428 trailing edge
3430 entry side surface
3432 side surface
3440 microphone
3442 accelerometer
3444 proximity sensor
3452 magnet ring
3454 coil
3456 movable portion
3457 aperture
3458 guiding portion
34610 vent aperture sizing control function A
34612 sizing control function A—step 1
34614 sizing control function A—step 5
34616 sizing control function A—step 3
34620 vent aperture sizing control function B
34622 sizing control function B—step 1
34623 sizing control function B—step 2*a*
34624 sizing control function B—step 2
34626 sizing control function B—step 3
34628 sizing control function B—step 4
34630 vent aperture sizing control function C 34631 sizing control function C—step 1a
34632 sizing control function C—step 1
34634 sizing control function C—step 2
34636 sizing control function C—step 3
34638 sizing control function C—step 4
34640 vent aperture sizing control function D
34641 sizing control function D—step 1a
34642 sizing control function D—step 1
34644 sizing control function D—step 2
34650 vent aperture sizing control function E
34651 sizing control function C—step 1a
34652 sizing control function C—step 1
34653 sizing control function C—step 2
34654 sizing control function C—step 3
34655 sizing control function C—step 4
34656 sizing control function C—step 4
34710 first calibration cycle
34712 first calibration cycle—step 1
34714 first calibration cycle—step 2
34716 first calibration cycle—step 3
34717 first calibration cycle—step 4
34718 first calibration cycle—step 5
34720 second calibration cycle
34722 second calibration cycle—step 1
34724 second calibration cycle—step 2
34726 second calibration cycle—step 3
34727 second calibration cycle—step 4
34728 second calibration cycle—step 5
3480 actuator
3510 swivel
3520 hall and socket
3600 connection port
3700 forehead support
4170 air circuit
4322 adjustable vent aperture

The invention claimed is:

1. A gas washout vent arrangement for exhausting a flow of exhaust gas received within a patient interface, the gas washout vent arrangement comprising:
   one or more vents to exhaust a flow of exhaust gas received within a patient interface, the one or more vents adapted to provide a plurality of different venting configurations; and
   a sensor adapted to generate a signal indicative of at least one of (i) a level of noise caused by the exhaust gas and (ii) an orientation of the patient interface,
   wherein the one or more vents are adjustable to one of the plurality of different venting configurations based on the signal.

2. The gas washout vent arrangement as claimed in claim 1, wherein the one or more vents are configured for continuous adjustment while the patient interface is in use.

3. The gas washout vent arrangement as claimed in claim 1, wherein the one or more vents are configured to adjust to vary at least one of (i) direction or (ii) velocity of the flow of exhausted gas.

4. The gas washout vent arrangement as claimed in claim 1, wherein the signal is based on at least one of (i) a measured noise level or (ii) a detected orientation of the patient interface.

5. The gas washout vent arrangement as claimed in claim 1, wherein the one or more vents are configured to adjust to vary one or more flow impedances of the one or more vents.

6. The gas washout vent arrangement as claimed in claim 1, wherein the one or more vents are configured to adjust by actuating movement of a movable portion of the one or more vents.

7. The gas washout vent arrangement as claimed in claim 1, wherein at least a portion of the gas washout vent arrangement is located in a patient interface or in an air circuit.

8. The gas washout vent arrangement as claimed in claim 1, further comprising a controller configured to selectively adjust the gas washout vent arrangement based on at least one of (i) a detected vent noise or (ii) a detected orientation of the patient interface, to increase an exhaust area of a first vent and decrease an exhaust area of a second vent.

9. Apparatus for treating a respiratory disorder comprising:
   a patient interface for delivering a supply of air or breathable gas to the entrance of a patient's airways;
   a flow generator for supplying the supply of air or breathable gas to the patient interface;
   a gas washout vent arrangement as claimed in claim 1; and
   a controller configured to receive the signal from the sensor and generate one or more signals to adjust the one or more vents in response to the signal indicative of the level of noise.

10. A control method of an apparatus for adjusting a flow of exhaust gas from a patient interface, the control method comprising:
    generating with a sensor a signal indicative of at least one of (i) a level of noise caused by a flow of exhaust gas through one or more vents from a patient interface, and (ii) an orientation of the patient interface causing the flow of exhaust gas through the one or more vents to flow from the patient interface in a given direction, the one or more vents adapted for a plurality of different venting configurations; and
    adjusting with a controller the one or more vents to one of the plurality of different venting configurations based on the signal, whereby the level of noise may be reduced.

11. The method claimed in claim 10, wherein the one or more vents are adapted for continuous adjustment while the patient interface is in use.

12. The method claimed in claim 10, wherein the adjusting the one or more vents to one of the plurality of different venting configurations changes a characteristic of the flow of exhaust gas.

13. The method claimed in claim 12, wherein the characteristic is at least one of direction or velocity of the flow of exhausted gas.

14. The method claimed in claim 10, wherein the signal is generated based on at least one of a measured noise level or detected orientation of the patient interface.

15. The method as claimed in claim 14, wherein the controller selectively adjusts the one or more vents based on the signal to increase an exhaust area of a first vent and decrease an exhaust area of a second vent.

16. The method claimed in claim 10, wherein the adjusting the one or more vents to one of the plurality of different venting configurations comprises actuating movement of a movable portion of the one or more vents.

17. An apparatus for delivering a flow of breathable gas to an airway of a user, the apparatus comprising:
    a plenum chamber, the plenum chamber adapted for coupling with a respiratory pressure therapy device to receive a supply of breathable gas to the plenum chamber, the plenum chamber further adapted to couple with the airway of the user; and one or more exhaust vents, the one or more exhaust vents coupled with the plenum chamber to permit a flow of exhaust gas from a cavity of the plenum chamber;

wherein the one or more exhaust vents are configured to change a direction of exhaust flow relative to the plenum chamber in accordance with orientation of the plenum chamber.

18. The apparatus of claim 17 wherein the one or more exhaust vents are configured to enforce an upward flow of exhaust gas from the plenum chamber upon a change to an orientation of the plenum chamber.

19. The apparatus of claim 17 wherein the one or more exhaust vents are configured to reduce the flow of exhaust gas in a direction of a bed partner upon a change to the orientation of the plenum chamber.

20. The apparatus of claim 17 wherein the one or more exhaust vents comprises a plurality of apertures and a movable portion configured to selectively move between a first end and a second end according to a gravitational orientation of the plenum chamber.

21. The apparatus of claim 17 further comprising an orientation sensor to generate a signal indicative of orientation of the plenum chamber, an actuator to adjust an opening of the one or more exhaust vents, and a controller coupled with the orientation sensor and the actuator, the controller configured to control adjustment of the opening of the one or more exhaust vents in response to the signal indicative of orientation of the plenum chamber.

22. The apparatus of claim 17 wherein the one or more exhaust vents comprises a first exhaust vent and a second exhaust vent, the first exhaust vent and the second exhaust vent located on opposing sides of the plenum chamber to direct the flow of exhaust gas in opposing directions.

23. The apparatus of claim 17 wherein the apparatus further comprises the respiratory pressure therapy device and a respiratory pressure therapy device controller including a processor, the respiratory pressure therapy device controller configured to control adjustment of an opening of the one or more exhaust vents.

24. The apparatus of claim 17 wherein a controller is configured to adjust the one or more vents based on a detected orientation of the plenum chamber to increase an exhaust area of a first vent and decrease an exhaust area of a second vent.

25. The apparatus of claim 17, wherein the plenum chamber forms a part of a patient interface.

\* \* \* \* \*